(12) United States Patent
Merla et al.

(10) Patent No.: US 7,696,238 B2
(45) Date of Patent: Apr. 13, 2010

(54) SUBSTITUTED BENZO[D]ISOXAZOL-3-YL AMINE COMPOUNDS AS ANALGESICS

(75) Inventors: Beatrix Merla, Aachen (DE); Robert Frank, Aachen (DE); Gregor Bahrenberg, Aachen (DE); Wolfgang Schroeder, Aachen (DE); Saskia Zemolka, Constance (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 11/941,331

(22) Filed: Nov. 16, 2007

(65) Prior Publication Data

US 2008/0176915 A1    Jul. 24, 2008

Related U.S. Application Data

(63) Continuation of application No. PCT/EP2006/004700, filed on May 18, 2006.

(30) Foreign Application Priority Data

May 18, 2005   (DE) .................. 10 2005 023 589
Aug. 16, 2005  (DE) .................. 10 2005 038 947

(51) Int. Cl.
   *A61K 31/423* (2006.01)
(52) U.S. Cl. ...................... 514/379; 548/241
(58) Field of Classification Search ............... 548/240, 548/241, 247; 514/379
See application file for complete search history.

(56) References Cited

U.S. PATENT DOCUMENTS

| | | | |
|---|---|---|---|
| 5,328,920 A * | 7/1994 | Effland et al. ............... | 514/339 |
| 6,352,999 B1 * | 3/2002 | Kennis et al. ............... | 514/291 |
| 2002/0128277 A1 | 9/2002 | Dworetzky et al. | |
| 2002/0156120 A1 | 10/2002 | Hewawasam et al. | |
| 2002/0193597 A1 | 12/2002 | McNaughton-Smith et al. | |

FOREIGN PATENT DOCUMENTS

| | | | | |
|---|---|---|---|---|
| WO | WO 92/17475 | * | 10/1992 | ................. 548/100 |
| WO | WO 94/12495 | * | 6/1994 | ................. 548/100 |
| WO | WO 96/39405 | * | 12/1996 | ................. 548/100 |
| WO | WO 02/066036 A1 | | 8/2002 | |
| WO | WO 03/040113 A1 | | 5/2003 | |
| WO | WO 2005/089753 | * | 9/2005 | ................. 548/100 |

OTHER PUBLICATIONS

Patani, George A. Bioisosterism: A rational approach in drug design. Chem. Rev. 96 (1996) 3147-3176.*

Fink, David M. Preparation of 3-(4-Pyridinylamino)-1,2-Benzisoxazoles via a Nucleophilic Aromatic Substitution Reaction. Tetrahedron Letters. 37(7) (1996) 995-998.*

Morissette et al. Advanced Drug Delivery Reviews 2004, 56, 275-300.*

Vippagunta et al., abstract, Vippagunta, Sudha R. "Crystalline Solids." Advanced Drug Delivery Reviews 48(2001): 3-26.*

Villalobos, Anabella. Novel Benzisoxazole Derivatives as Potent and Selective Inhibitors of Acetylcholinesterase. J. Med. Chem. 37 (1994) 2721-2734.*

Tong, Weida. A Comparative Molecular Filed Analysis Study of N-Benzylpiperidine as Acetylcholinesterase Inhibitors, J. Med. Chem. 39 (1996) 380-387.*

Bernard, Philippe. Automated docking of 82 N-benzylpiperidine derivatives to mouse Acetylcholinesterase and comparative molecular field analysis with 'natural' alignment. Journal of Computer-Aided Molecular Design, 13 (1999) 355-371.*

Golbraikh, Alexander. Validation of protein-based alignment in 3D quantitative structure-activity relationships with CoMFA models. Eur. J. Med. Chem. 35 (2000) 123-136.*

Guo, Jianxin. A docking score function for estimating ligand-protein interactions: application to acetylcholinesterase inhibition. J. Med. Chem. 47 (2004) 5492-5500.*

Kandemirli, F. Human Acetylcholinesterase Inhibitors: Electronic-Topological and Neural Network Approaches to the structure-activity relationships study. Mini-Reviews in Medicinal Chemistry-. 5 (2005) 479-487.*

International Search Report dated Aug. 28, 2006 with English translation (Four (4) Pages).

International Preliminary Report PCT/IPEA/409 dated Sep. 13, 2007 with English translation of relevant portion (Seven (7) Pages).

* cited by examiner

*Primary Examiner*—Kamal A Saeed
*Assistant Examiner*—Samantha L Shterengarts
(74) *Attorney, Agent, or Firm*—Crowell & Moring LLP

(57) ABSTRACT

Substituted benzo[d]isoxazol-3-yl amine compounds corresponding to formula I

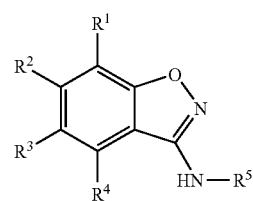

which exhibit an strong affinity to the KCNQ2/3 $K^+$ channel, and which are suitable for treating or inhibiting pain and/or disorders or disease states that are at least partly mediated by the KCNQ2/3 $K^+$ channel.

15 Claims, No Drawings

SUBSTITUTED BENZO[D]ISOXAZOL-3-YL AMINE COMPOUNDS AS ANALGESICS

CROSS REFERENCE TO RELATED APPLICATIONS

This application is a continuation of international patent application no. PCT/EP2006/004700, filed May 18, 2006 designating the United States of America, and published on Nov. 23, 2006 as WO 2006/122800, the entire disclosure of which is incorporated herein by reference. Priority is claimed based on German patent application nos. DE 10 2005 023 589.1, filed May 18, 2005 and DE 10 2005 038 947.3, filed Aug. 16, 2005.

BACKGROUND OF THE INVENTION

The present invention relates to substituted benzo(d)isoxazol-3-yl amine compounds, processes for their production, medicaments containing these compounds, as well as the use of these compounds for the production of medicaments.

The treatment of pain, in particular neuropathic pain, is extremely important in medicine. There is therefore a universal need for effective pain treatments. The urgent need for a patient-friendly and target-oriented treatment of chronic and non-chronic pain states, by which is understood the treatment of pain which is successful and satisfactory for the patient, is also documented in the large number of scientific articles and papers that have recently appeared in the field of applied analgesics and basic research in nociception.

A pathophysiological feature of chronic pain is the over-excitability of neurons. Neuronal excitability is decisively influenced by the activity of K$^+$ channels, since these decisively determine the resting membrane potential of the cell and thus the excitability threshold. Heteromeric K$^+$ channels from the molecular subtype KCNQ2/3 (Kv7.2/7.3) are expressed in neurons of various regions of the central nervous system (hippocampus, amygdala) and peripheral nervous system (posterior dorsal root ganglia) and regulate their excitability. The activation of KCNQ2/3 K$^+$ channels leads to a hyperpolarisation of the cell membrane and, concomitantly, to a decrease in the electrical excitability of these neurons. KCNQ2/3-expressing neurons of the posterior dorsal root ganglia are involved in the transmission of nociceptive stimuli from the periphery to the spinal cord (Passmore et al., 2003). Accordingly, an analgesic effectiveness could be detected for the KCNQ2/3 agonist retigabin in preclinical neuropathic pain and inflammatory pain models (Blackburn-Munro and Jensen, 2003; Passmore et al., 2003; Dost et al., 2004). The KCNQ2/3 K$^+$ channel is thus a suitable starting point for the treatment of pain, in particular pain selected from the group consisting of chronic pain, neuropathic pain, inflammatory pain and muscular pain (Nielsen et al., 2004), especially neuropathic and inflammatory pain. Moreover, the KCNQ2/3 K$^+$ channel is a suitable target for the treatment of a large number of further medical conditions, such as for example migraine (US2002/0128277), cognitive disorders (Gribkoff, 2003), anxiety states (Korsgaard et al., 2005), epilepsy (Wickenden et al. 2004) and urinary incontinence (Streng et al. 2004).

SUMMARY OF THE INVENTION

It is an object of the invention to provide new compounds that are suitable in particular as pharmacological active substances in medicaments.

Another object of the invention is to provide compounds which are particularly suited for treating or inhibiting disorders or diseases which are at least partly mediated by KCNQ2/3 K$^+$ channels.

These and other objects are achieved in accordance with the present invention by providing a substituted benzo[d] isoxazol-3-yl amine compound corresponding to formula I

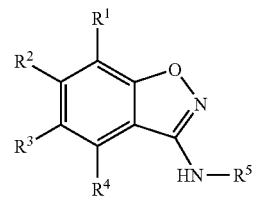

wherein
$R^1$, $R^2$, $R^3$ and $R^4$ each independently denote H, F, Cl, Br, I, —CN, —NO$_2$, —SF$_5$, —NR$^7$R$^8$, —OR$^9$, —SR$^{10}$, —C(=O)OR$^{11}$, —C(=O)NR$^{12}$R$^{13}$, —S(=O)$_2$R$^{14}$, —C(=O)R$^{15}$, —NR$^{16}$—S(=O)$_2$R$^{17}$, C$_{1-10}$-alkyl, C$_{2-10}$-alkenyl, or C$_{2-10}$-alkinyl;

$R^5$ denotes —C(=S)NR$^{21}$R$^{22}$ or (CHR$^6$)$_n$—R$^{25}$, wherein n=1, 2 or 3;

$R^6$ denotes H, C$_{3-8}$-cycloalkyl or C$_{1-6}$-alkyl, and $R^{25}$ denotes aryl or heteroaryl;

$R^7$ and $R^8$ each independently denote H, —C(=O)R$^{14}$ or C$_{1-10}$-alkyl, or $R^7$ and $R^8$ together with the nitrogen atom to which they are bound form a morpholine, piperidine or pyrrolidine ring;

$R^9$, $R^{10}$, $R^{11}$ and $R^{16}$ each independently denote H, C$_{1-10}$-alkyl, C$_{2-10}$-alkenyl, C$_{2-10}$-alkinyl, C$_{3-8}$-cycloalkyl, —(C$_{1-5}$-alkylene)-C$_{3-8}$-cycloalkyl, heterocycloalkyl, —(C$_{1-5}$-alkylene)-heterocycloalkyl, aryl, heteroaryl, —(C$_{1-5}$-alkylene)-aryl, or —(C$_{1-5}$-alkylene)-heteroaryl;

$R^{12}$ and $R^{13}$ each independently denote H or C$_{1-10}$-alkyl, or $R^{12}$ and $R^{13}$ together with the nitrogen atom to which they are bound form a morpholine, piperidine or pyrrolidine ring;

$R^{14}$ denotes —NR$^7$R$^8$, C$_{1-10}$-alkyl, C$_{2-10}$-alkenyl, C$_{2-10}$-alkinyl, C$_{3-8}$-cycloalkyl, —(C$_{1-5}$-alkylene)-C$_{3-8}$-cycloalkyl, heterocycloalkyl, —(C$_{1-5}$-alkylene)-heterocycloalkyl, aryl, heteroaryl, —(C$_{1-5}$-alkylene)-aryl or —(C$_{1-5}$-alkylene)-heteroaryl;

$R^{15}$ and $R^{17}$ each independently denote C$_{1-10}$-alkyl, C$_{2-10}$-alkenyl, C$_{2-10}$-alkinyl, C$_{3-8}$-cycloalkyl, —(C$_{1-5}$-alkylene)-C$_{3-8}$-cycloalkyl, heterocycloalkyl, —(C$_{1-5}$-alkylene)-heterocycloalkyl, aryl, heteroaryl, —(C$_{1-5}$-alkylene)-aryl or —(C$_{1-5}$-alkylene)-heteroaryl;

$R^{21}$ and $R^{22}$ each independently denote H, C$_{1-10}$-alkyl, C$_{2-10}$-alkenyl, C$_{2-10}$-alkinyl, C$_{3-8}$-cycloalkyl, —(C$_{1-5}$-alkylene)-C$_{3-8}$-cycloalkyl, heterocycloalkyl, —(C$_{1-5}$-alkylene)-heterocycloalkyl, aryl, heteroaryl, —(C$_{1-5}$-alkylene)-aryl or —(C$_{1-5}$-alkylene)-heteroaryl;

wherein
the aforementioned C$_{1-10}$-alkyl, C$_{2-10}$-alkenyl and C$_{2-10}$-alkinyl groups may each be linear or branched and may optionally be substituted with 1, 2, 3, 4 or 5 substituents independently selected from the group consisting of F, Cl, Br, COOH, COOC$_{1-4}$-alkyl, —CN, —OH, —SH, —O—C$_{1-2}$-alkyl, —S—C$_{1-2}$-alkyl and —NH$_2$;

the aforementioned C$_{3-8}$-cycloalkyl groups may each optionally be substituted with 1, 2, 3, 4 or 5 substituents independently selected from the group consisting of F, Cl, Br, —CN, —OH, —SH, —$C_{1-5}$-alkyl, —O—$C_{1-2}$-alkyl, —S—$C_{1-2}$-alkyl and —$NH_2$;

the aforementioned heterocycloalkyl groups each comprise a 4-, 5-, 6- or 7-membered ring containing 1 or 2 heteroatoms independently selected from the group consisting of oxygen, sulfur and nitrogen, and may optionally be substituted with 1, 2, 3, 4 or 5 substituents independently selected from the group consisting of F, Cl, Br, —CN, —OH, —SH, —$C_{1-5}$-alkyl, —O—$C_{1-2}$-alkyl, —S—$C_{1-2}$-alkyl and —$NH_2$;

the aforementioned aryl groups each independently denote a phenyl, anthracenyl or naphthyl group, which optionally may be substituted with 1, 2, 3, 4 or 5 substituents independently selected from the group consisting of F, Cl, Br, I, —$CF_3$, —$OCF_3$, —$SCF_3$, $C(=O)C_{1-5}$-alkyl,

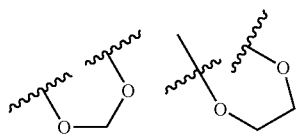

—$NO_2$, cyclohexyl, —$SF_5$, —CN, —OH, —SH, —$C_{1-5}$-alkyl, —O—$C_{1-5}$-alkyl, —S—$C_{1-5}$-alkyl, —C(=O)—OH, —O(C=O)$C_{1-2}$-alkyl, —C(=O)—O$C_{1-5}$-alkyl, —$NH_2$, —N(H)($C_{1-5}$-alkyl), —N($C_{1-5}$-alkyl)($C_{1-5}$-alkyl), —C(=O)$NH_2$, —C(=O)N(H)($C_{1-5}$-alkyl), —C(=O)N($C_{1-5}$-alkyl)($C_{1-5}$-alkyl), —S(=O)$_2NH_2$, —S(=O)$_2$N(H)($C_{1-5}$-alkyl), —S(=O)$_2$N($C_{1-5}$-alkyl)($C_{1-5}$-alkyl), —S(=O)$_2$-phenyl, —S(=O)$_2$—$C_{1-5}$-alkyl, phenyl, phenoxy, benzyl, benzyloxy, thiophenyl (thienyl), furanyl and pyridinyl; and the aforementioned heteroaryl groups each independently comprise a 5- or 6-membered ring containing 1, 2 or 3 heteroatoms independently selected from the group consisting of oxygen, sulfur and nitrogen, and may optionally be substituted with 1, 2, 3, 4 or 5 substituents independently selected from the group consisting of F, Cl, Br, I, —$CF_3$, —$OCF_3$, —$SCF_3$, —$SF_5$, —CN, —OH, —SH, —$C_{1-5}$-alkyl, —O—$C_{1-5}$-alkyl, —S—$C_{1-5}$-alkyl, —C(=O)—OH, —C(=O)—O$C_{1-5}$-alkyl, —$NH_2$, —N(H)($C_{1-5}$-alkyl), —N($C_{1-5}$-alkyl)($C_{1-5}$-alkyl), —C(=O)$NH_2$, —C(=O)N(H)($C_{1-5}$-alkyl), —C(=O)N($C_{1-5}$-alkyl)($C_{1-5}$-alkyl), —S(=O)$_2NH_2$, —S(=O)$_2$N(H)($C_{1-5}$-alkyl), —S(=O)$_2$N($C_{1-5}$-alkyl)($C_{1-5}$-alkyl), —S(=O)$_2$-phenyl, —S(=O)$_2$—$C_{1-5}$-alkyl, phenyl, phenoxy, benzyl, thiophenyl (thienyl), furanyl and pyridinyl;

or a pharmaceutically acceptable salt or solvate thereof.

It has now surprisingly been found that substituted benzo(d)isoxazol-3-yl amine compounds corresponding to formula I given below are suitable for the treatment of pain and also have an excellent affinity for the KCNQ2/3 $K^+$ channel, and are therefore suitable for the treatment of disorders or diseases which are at least partly mediated by KCNQ2/3 $K^+$ channels.

The present invention accordingly provides substituted benzo(d)isoxazol-3-yl amine compounds corresponding to formula I

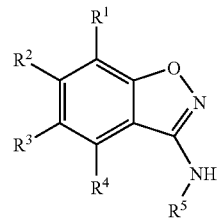

wherein
$R^1$, $R^2$, $R^3$ and $R^4$ each denote, independently of one another:
H, F, Cl, Br, I, —CN, —$NO_2$, —$SF_5$, —$NR^7R^8$, —$OR^9$, —$SR^{10}$, —C(=O)$OR^{11}$, —(C=O)$NR^{12}R^{13}$, —S(=O)$_2R^{14}$, —C(=O)$R^{15}$, —$NR^{16}$—S(=O)$_2R^{17}$; or a linear or branched, saturated or unsaturated, unsubstituted or mono- or polysubstituted aliphatic group;

a saturated or unsaturated, unsubstituted or mono- or polysubstituted cycloaliphatic group optionally containing at least one heteroatom as ring member, which optionally can be condensed with a monocyclic or polycyclic ring system, and/or which optionally can be bonded via a linear or branched alkylene, alkenylene or alkinylene group; or an unsubstituted or mono- or polysubstituted aryl or heteroaryl group, which optionally can be condensed with a monocyclic or polycyclic ring system, and/or which optionally can be bonded via a linear or branched alkylene, alkenylene or alkinylene group;

$R^5$ denotes
—C(=S)$NR^{21}R^{22}$, or
a linear or branched, saturated or unsaturated, unsubstituted or mono- or polysubstituted aliphatic group; or
an unsubstituted or mono- or polysubstituted aryl or heteroaryl group, which optionally can be condensed with a monocyclic or polycyclic ring system, and which is bonded via a linear or branched alkylene group;

$R^7$ and $R^8$ each denote, independently of one another:
H, —C(=O)$R^{15}$, or a linear or branched, saturated or unsaturated, unsubstituted or mono- or polysubstituted aliphatic group, or $R^7$ and $R^8$ together with the nitrogen atom joining them as ring member form a saturated or unsaturated, unsubstituted or mono- or polysubstituted heterocycloaliphatic group, optionally containing at least one further heteroatom as ring member;

$R^9$, $R^{10}$, $R^{11}$ and $R^{16}$ each denote, independently of one another, H; or a linear or branched, saturated or unsaturated, unsubstituted or mono- or polysubstituted aliphatic group;

a saturated or unsaturated, unsubstituted or mono- or polysubstituted cycloaliphatic group, optionally containing at least one heteroatom as ring member, which optionally can be condensed with a monocyclic or polycyclic ring system, and/or which optionally can be bonded via a linear or branched alkylene group; or an unsubstituted or mono- or polysubstituted aryl or heteroaryl group, which optionally can be condensed with a monocyclic or polycyclic ring system, and/or which optionally can be bonded via a linear or branched alkylene group;

$R^{12}$ and $R^{13}$ each denote, independently of one another, H or a linear or branched, saturated or unsaturated, unsubstituted or mono- or polysubstituted aliphatic group, or $R^{12}$ and $R^{13}$ together with the nitrogen atom joining them as ring member form a saturated or unsaturated, unsubstituted or mono- or polysubstituted heterocycloaliphatic group, optionally containing at least one further heteroatom as ring member;

$R^{14}$ denotes

—$NR^7R^8$;

a linear or branched, saturated or unsaturated, unsubstituted or mono- or polysubstituted aliphatic group;

a saturated or unsaturated, unsubstituted or mono- or polysubstituted cycloaliphatic group, optionally containing at least one heteroatom as ring member, which optionally can be condensed with a monocyclic or polycyclic ring system, and/or which optionally can be bonded via a linear or branched alkylene group; or an unsubstituted or mono- or polysubstituted aryl or heteroaryl group, which optionally can be condensed with a monocyclic or polycyclic ring system and/or which optionally can be bonded via a linear or branched alkylene group;

$R^{15}$ and $R^{17}$ each denote, independently of one another:

a linear or branched, saturated or unsaturated, unsubstituted or mono- or polysubstituted aliphatic group;

a saturated or unsaturated, unsubstituted or mono- or polysubstituted cycloaliphatic group, optionally containing at least one heteroatom as ring member, which optionally can be condensed with a monocyclic or polycyclic ring system, or which optionally can be bonded via a linear or branched alkylene group, or both; or an unsubstituted or mono- or polysubstituted aryl or heteroaryl group, which optionally can be condensed with a monocyclic or polycyclic ring system, or which optionally can be bonded via a linear or branched alkylene group, or both;

$R^{21}$ and $R^{22}$, each denote, independently of one another:

H;

a linear or branched, saturated or unsaturated, unsubstituted or mono- or polysubstituted aliphatic group;

a saturated or unsaturated, unsubstituted or mono- or polysubstituted cycloaliphatic group optionally containing at least one heteroatom as ring member, which optionally can be condensed with a monocyclic or polycyclic ring system, or which optionally can be bonded via a linear or branched alkylene group, or both; or an unsubstituted or mono- or polysubstituted aryl or heteroaryl group, which optionally can be condensed with a monocyclic or polycyclic ring system, and/or which optionally can be bonded via a linear or branched alkylene group;

in the form of the racemate; in the form of the enantiomers, diastereomers, mixtures of the enantiomers or diastereomers, or in the form of an individual enantiomer or diastereomer; in the form of the bases and/or salts of physiologically compatible acids.

Preferably the aforementioned (hetero)cycloaliphatic groups can optionally be substituted in each case with 1, 2, 3, 4 or 5 substituents selected independently of one another from the group consisting of oxo (=O), thioxo (=S), F, Cl, Br, I, —CN, —$CF_3$, —$SF_5$, —OH, —O—$C_{1-5}$-alkyl, —$NH_2$, —$NO_2$, —O—$CF_3$, S—$CF_3$, —SH, —S—$C_{1-5}$ alkyl, —$C_{1-5}$-alkyl, —C(=O)—OH, —C(=O)—O—$C_{1-5}$-alkyl, —NH—$C_{1-5}$-alkyl, —N($C_{1-5}$-alkyl)$_2$, —O-phenyl, —O-benzyl, phenyl and benzyl, wherein in each case the cyclic part of the groups —O-phenyl, —O-benzyl, phenyl and benzyl can be substituted with 1, 2, 3, 4 or 5 substituents selected independently of one another from the group consisting of F, Cl, Br, —OH, —$CF_3$, —$SF_5$, —CN, —$NO_2$, —$C_{1-5}$ alkyl, —O—$C_{1-5}$ alkyl, —O—$CF_3$, —S—$CF_3$, phenyl and —O-benzyl. If a cycloaliphatic group contains one or more, for example 1, 2, 3, 4 or 5 heteroatoms as ring members, then these can preferably be selected independently of one another from the group consisting of oxygen, nitrogen and sulfur.

Examples of (hetero)cycloaliphatic groups that may be mentioned include cyclopropyl, cyclobutyl, cyclopentyl, cyclohexyl, cycloheptyl, cyclooctyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl and dithiolanyl.

A monocyclic or polycyclic ring system is understood in the context of the present invention to mean monocyclic or polycyclic hydrocarbon groups, which are saturated or unsaturated and can optionally contain 1, 2, 3, 4 or 5 heteroatom(s) as ring member(s), which independently of one another are selected from the group consisting of oxygen, nitrogen and sulfur. Such a monocyclic or polycyclic ring system can for example be condensed (annelated) to an aryl group or to a heteroaryl group.

If a polycyclic ring system, such as for example a bicyclic ring system is present, the various rings can, in each case independently of one another, have a different degree of saturation, i.e. can be saturated or unsaturated. A bicyclic ring system is preferred.

Examples of aryl groups that are condensed with a monocyclic or polycyclic ring system include (1,3)-benzodioxolyl and (1,4)-benzodioxanyl.

Preferably the rings of the aforementioned monocyclic or polycyclic ring system are in each case 5-, 6- or 7-membered rings and can in each case optionally contain 1, 2, 3, 4 or 5 heteroatom(s) as ring member(s), which are selected independently of one another from the group consisting of oxygen, nitrogen and sulfur.

Also preferably, the rings of the aforementioned monocyclic or polycyclic ring systems can optionally be substituted in each case with 1, 2, 3, 4 or 5 substituents selected independently of one another from the group consisting of oxo (=O) thioxo (=S), F, Cl, Br, I, —CN, —$CF_3$, —$SF_5$, —OH, —O—$C_{1-5}$-alkyl, O—$C_{1-5}$-alkyl, —$NH_2$, —$NO_2$, —O—$CF_3$, S—$CF_3$, —SH, —S—$C_{1-5}$-alkyl, —$C_{1-5}$-alkyl, —C(=O)—OH, —C(=O)—O—$C_{1-5}$-alkyl, —NH—$C_{1-5}$-alkyl, —N($C_{1-5}$-alkyl)$_2$, —O-phenyl, —O-benzyl, phenyl and benzyl, wherein in each case the cyclic part of the groups —O-phenyl, —O-benzyl, phenyl and benzyl can be substituted with 1, 2, 3, 4 or 5 substituents selected independently of one another from the group consisting of F, Cl, Br, —OH, —$CF_3$, —$SF_5$, —CN, —$NO_2$, —$C_{1-5}$ alkyl, —O—$C_{1-5}$ alkyl, —O—$CF_3$, —S—$CF_3$, phenyl and —O-benzyl.

Also preferably, the aforementioned aryl or heteroaryl groups can optionally be substituted in each case with 1, 2, 3, 4 or 5 substituents selected independently of one another from the group consisting of F, Cl, Br, I, —CN, —$CF_3$, —$SF_5$, —OH, —O—$C_{1-5}$-alkyl, —$NH_2$, —$NO_2$, —O—$CF_3$, S—$CF_3$, —SH, —S—$C_{1-5}$-alkyl, —$C_{1-5}$-alkyl, —C(=O)—OH, —C(=O)—O—$C_{1-5}$ alkyl, —NH—$C_{1-5}$-alkyl, —N($C_{1-5}$-alkyl)$_2$, —NH—C(=O)—O—$C_{1-5}$-alkyl, —C(=O)—H, —O(C=O)—$C_{1-5}$-alkyl, —C(=O)—$C_{1-5}$-alkyl, —C(=O)—$NH_2$, —C(=O)NH—$C_{1-5}$-alkyl, —C(=O)—N($C_{1-5}$-alkyl)$_2$, —S(=O)$_2NH_2$; —S(=O)$_2$N(H)($C_{1-5}$-alkyl); —S(=O)$_2$N($C_{1-5}$-alkyl)($C_{1-5}$-alkyl);

—S(=O)$_2$phenyl; —S(=O)$_2$—C$_{1-5}$-alkyl; cyclohexyl; cyclopentyl; —O-phenyl, —O-benzyl, phenyl and benzyl, wherein in each case the cyclic part of the groups —O-phenyl, —O-benzyl, phenyl, cyclohexyl, cyclopentyl, —S(=O)$_2$phenyl and benzyl can be substituted with 1, 2, 3, 4 or 5 substituents selected independently of one another from the group consisting of F, Cl, Br, —OH, —CF$_3$, —CN, —NO$_2$, —C$_{1-5}$-alkyl, —O—C$_{1-5}$-alkyl, —O—CF$_3$, —S—CF$_3$, phenyl and —O-benzyl.

Also preferably, the aforementioned heteroaryl groups in each case contain 1, 2, 3, 4 or 5 heteroatom(s) selected independently of one another from the group consisting of oxygen, nitrogen and sulfur as ring member(s).

Examples of aryl groups include phenyl and naphthyl (including 1-naphthyl and 2-naphthyl).

Examples of heteroaryl groups include thiophenyl, furanyl, pyrrolyl, pyrazolyl, pyrazinyl, pyranyl, triazolyl, pyridinyl, imidazolyl, indolyl, isoindolyl, benzo(b)furanyl, benzo(b)thiophenyl, thiazolyl, oxazolyl, isoxazolyl, pyridazinyl, pyrazinyl, pyrimidinyl, indazolyl, quinoxalinyl, quinolinyl and isoquinolinyl.

The aforementioned aliphatic groups, i.e. the alkyl, alkenyl and alkinyl groups, can preferably contain 1-10 or 2-10 carbon atoms in the alkyl part and can preferably be substituted with optionally 1, 2, 3, 4, 5, 6, 7, 8 or 9 substituents selected independently of one another from the group consisting of F, Cl, Br, I, —CN, —NO$_2$, —OH, —NH$_2$, —SH, —O(C$_{1-5}$-alkyl), —S(C$_{1-5}$-alkyl), —NH(C$_{1-5}$-alkyl), —N(C$_{1-5}$-alkyl)(C$_{1-5}$-alkyl), OCF$_3$, C$_{3-8}$-cycloalkyl and —SCF$_3$. Alkenyl groups contain at least one, preferably 1, 2, 3 or 4 C—C double bonds, and alkinyl groups contain at least one, preferably 1, 2, 3 or 4 C—C triple bonds.

Preferred are alkyl groups selected from the group consisting of methyl, ethyl, n-propyl, isopropyl, n-butyl, sec-butyl, isobutyl, tert-butyl, n-pentyl, sec-pentyl, neopentyl and n-hexyl, which can optionally be substituted with 1, 2, 3, 4, 5, 6, 7, 8 or 9 substituents selected independently of one another from the group consisting of F, Cl, Br, I, —CN, —NO$_2$, —OH, —NH$_2$, —SH, —OCH$_3$, —O—C$_2$H$_5$, —SCH$_3$, —S—C$_2$H$_5$, —OCF$_3$, —SCF$_3$, —NH—CH$_3$, —N(CH$_3$)$_2$, —N(C$_2$H$_5$)$_2$ and —N(CH$_3$)(C$_2$H$_5$).

Also preferred are alkenyl groups selected from the group consisting of vinyl, 1-propenyl, 2-propenyl, 1-butenyl, 2-butenyl, 3-butenyl, 2-methyl-buten-2-yl, 1-pentenyl, 2-pentenyl, 3-pentenyl and 4-pentenyl, which can optionally be substituted with 1, 2 or 3 substituents selected independently of one another from the group consisting of F, Cl, Br, I, —CN, —NO$_2$, —OH, —NH$_2$, —SH, —OCH$_3$, —O—C$_2$H$_5$, —SCH$_3$, —S—C$_2$H$_5$, —OCF$_3$, —SCF$_3$, —NH—CH$_3$, —N(CH$_3$)$_2$, —N(CH$_2$H$_5$)$_2$ and —N(CH$_3$)(C$_2$H$_5$).

Also preferred are alkinyl groups selected from the group consisting of ethinyl, 1-propinyl, 2-propinyl, 1-butinyl, 2-butinyl and 3-butinyl, which can optionally be substituted with 1, 2 or 3 substituents selected independently of one another from the group consisting of F, Cl, Br, I, —CN, —NO$_2$, —OH, —NH$_2$, —SH, —OCH$_3$, —O—C$_2$H$_5$, —SCH$_3$, —SC$_2$H$_5$, —OCF$_3$, —SCF$_3$, —NH—CH$_3$, —N(CH$_3$)$_2$, —N(C$_2$H$_5$)$_2$ and —N(CH$_3$)(C$_2$H$_5$).

Preferred are substituted benzo(d)isoxazol-3-yl amine compounds corresponding to formula I, in which:

$R^1$, $R^2$, $R^3$ and $R^4$ each denote, independently of one another:

H, F, Cl, Br, I, —CN, —NO$_2$, —SF$_5$, —NR$^7$R$^8$, —OR$^9$, —SR$^{10}$, —C(=O)R$^{11}$, —C(=O)NR$^{12}$R$^{13}$, —S(=O)$_2$R$^{14}$, —C(=O)R$^{15}$, —NR$^{16}$—S(=O)$_2$R$^{17}$, C$_{1-10}$-alkyl C$_{2-10}$-alkenyl, or C$_{2-10}$-alkinyl;

$R^5$ denotes —C(=S)NR$^{21}$R$^{22}$ or (CHR$^6$)$_n$—R$^{25}$, wherein:

n=1, 2 or 3, $R^6$ denotes H, C$_{3-8}$-cycloalkyl or C$_{1-6}$-alkyl, and $R^{25}$ denotes aryl or heteroaryl;

$R^7$ and $R^8$ each denote, independently of one another, H, —C(=O)R$^{14}$ or C$_{1-10}$-alkyl; or $R^7$ and $R^8$ together with the nitrogen atom joining them as ring member form a morpholine, piperidine or pyrrolidine group;

$R^9$, $R^{10}$, $R^{11}$ and $R^{16}$ each denote, independently of one another:

H, C$_{1-10}$-alkyl, C$_{2-10}$-alkenyl, C$_{2-10}$ alkinyl; C$_{3-8}$-cycloalkyl, —(C$_{1-5}$-alkylene)-C$_{3-8}$-cycloalkyl, heterocycloalkyl, —(C$_{1-5}$-alkylene)-heterocycloalkyl, aryl, heteroaryl, —(C$_{1-5}$-alkylene)-aryl, or —(C$_{1-5}$-alkylene)-heteroaryl;

$R^{12}$ and $R^{13}$ each denote, independently of one another, H or a C$_{1-10}$-alkyl group; or $R^{12}$ and $R^{13}$ together with the nitrogen atom joining them as ring member form a morpholine, piperidine or pyrrolidine group;

$R^{14}$ denotes —NR$^7$R$^8$; C$_{1-10}$-alkyl, C$_{2-10}$-alkenyl, C$_{2-10}$-alkinyl, C$_{3-8}$-cycloalkyl, —(C$_{1-5}$-alkylene)-C$_{3-8}$-cycloalkyl, heterocycloalkyl, —(C$_{1-5}$-alkylene)-heterocycloalkyl, aryl, heteroaryl, —(C$_{1-5}$-alkylene)-aryl, or —(C$_{1-5}$-alkylene)-heteroaryl;

$R^{15}$ and $R^{17}$ each denote, independently of one another, C$_{1-10}$-alkyl, C$_{2-10}$-alkenyl, C$_{2-10}$-alkinyl, C$_{3-8}$-cycloalkyl, —(C$_{1-5}$-alkylene)-C$_{3-8}$-cycloalkyl, heterocycloalkyl, —(C$_{1-5}$-alkylene)-heterocycloalkyl, aryl, heteroaryl, —(C$_{1-5}$-alkylene)-aryl, or —(C$_{1-5}$-alkylene)-heteroaryl;

$R^{21}$ and $R^{22}$ each denote, independently of one another, H, C$_{1-10}$-alkyl, C$_{2-10}$-alkenyl, C$_{2-10}$-alkinyl, C$_{3-8}$-cycloalkyl, —(C$_{1-5}$-alkylene)-C$_{3-8}$-cycloalkyl, heterocycloalkyl, —(C$_{1-5}$-alkylene)-heterocycloalkyl, aryl, heteroaryl, —(C$_{1-5}$-alkylene)-aryl, or —(C$_{1-5}$-alkylene)-heteroaryl;

wherein the aforementioned C$_{1-10}$-alkyl, C$_{2-10}$-alkenyl and C$_{2-10}$-alkinyl groups each may be linear or branched and can optionally be substituted with 1, 2, 3, 4 or 5 substituents selected independently from the group consisting of F, Cl, Br, COOH, COOC$_{1-4}$-alkyl, —CN, —OH, —SH, —O—C$_{1-2}$-alkyl, —S—C$_{1-2}$-alkyl, and —NH$_2$;

the aforementioned C$_{3-8}$-cycloalkyl groups each may optionally be substituted with 1, 2, 3, 4 or 5 substituents independently selected from the group consisting of F, Cl, Br, —CN, —OH, —SH, —C$_{1-5}$-alkyl, —O—C$_{1-12}$-alkyl, —S—C$_{1-2}$-alkyl and —NH$_2$;

the aforementioned heterocycloalkyl groups each may be a 4-, 5-, 6- or 7-membered ring containing 1 or 2 heteroatoms selected independently from the group consisting of oxygen, sulfur and nitrogen as ring member(s), and can optionally be substituted with 1, 2, 3, 4 or 5 substituents independently selected from the group consisting of F, Cl, Br, —CN, —OH, —SH, —C$_{1-5}$-alkyl, —O—C$_{1-2}$-alkyl, —S—C$_{1-2}$-alkyl and —NH$_2$;

the aforementioned aryl groups each denote a phenyl, anthracenyl or naphthyl group, which can be substituted with 1, 2, 3, 4 or 5 substituents independently selected from the group consisting of F, Cl, Br, I, —CF$_3$, —OCF$_3$, —SCF$_3$, C(=O)C$_{1-5}$-alkyl,

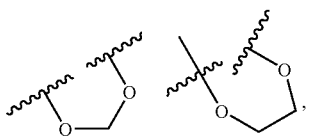

NO₂, cyclohexyl, —O(C=O)C₁₋₁₂-alkyl, —SF₅, —CN, —OH, —SH, —C₁₋₅-alkyl, —O—C₁₋₅-alkyl, —S—C₁₋₅-alkyl, —C(=O)—OH, —C(=O)—OC₁₋₅-alkyl, —NH₂, —N(H)(C₁₋₅-alkyl), —N(C₁₋₅-alkyl)(C₁₋₅-alkyl), —C(=O)NH₂, —C(=O)N(H)(C₁₋₅-alkyl), —C(=O)N(C₁₋₅-alkyl)(C₁₋₅-alkyl), —S(=O)₂NH₂, —S(=O)₂N(H)(C₁₋₅-alkyl), —S(=O)₂N(C₁₋₅-alkyl)(C₁₋₅-alkyl), —S(=O)₂-phenyl, —S(=O)₂—C₁₋₅-alkyl, phenyl, phenoxy, benzyl, benzyloxy, thiophenyl (thienyl), furanyl and pyridinyl;

the aforementioned heteroaryl groups each are 5- or 6-membered groups containing 1, 2 or 3 heteroatoms independently selected from the group consisting of oxygen, sulfur and nitrogen as ring member(s), and can optionally be substituted with 1, 2, 3, 4 or 5 substituents independently selected from the group consisting of F, Cl, Br, I, —CF₃, —OCF₃, —SCF₃, —SF₅, —CN, —OH, —SH, —C₁₋₅-alkyl, —O—C₁₋₅-alkyl, —S—C₁₋₅-alkyl, —C(=O)—OH, —C(=O)—OC₁₋₅-alkyl, —NH₂, —N(H)(C₁₋₅-alkyl), —N(C₁₋₅-alkyl)(C₁₋₅-alkyl), —C(=O)NH₂, —C(=O)N(H)(C₁₋₅-alkyl), —C(=O)N(C₁₋₅-alkyl)(C₁₋₅-alkyl), —S(=O)₂NH₂, —S(=O)₂N(H)(C₁₋₅-alkyl), —S(=O)₂N(C₁₋₅-alkyl)(C₁₋₅-alkyl), —S(=O)₂-phenyl, —S(=O)₂—C₁₋₅-alkyl, phenyl, phenoxy, benzyl, thiophenyl (thienyl), furanyl and pyridinyl;

in the form of the racemate; in the form of the enantiomers, diastereomers, mixtures of the enantiomers or diastereomers, or in the form of an individual enantiomer or diastereomer; in the form of the bases and/or salts of physiologically compatible acids.

Particularly preferred are compounds according to the invention of the formula I, wherein $R^1, R^2, R^3$ and $R^4$ each denote, independently of one another, H, F, Cl, Br, I, —CN, —NR⁷R⁸, —OR⁹, —SR¹⁰, $C_{1-4}$-alkyl, $C_{2-4}$-alkenyl or $C_{2-4}$-alkinyl;

$R^5$ denotes —C(=S)NR²¹R²² or —(CHR⁶)ₙ—R²⁵, wherein n=1, 2 or 3;

$R^6$ denotes H or $C_{1-6}$-alkyl, and $R^{25}$ denotes aryl or heteroaryl;

$R^7$ and $R^8$ each denote, independently of one another, H, —C(=O)R¹⁵ or $C_{1-4}$-alkyl, or $R^7$ and $R^8$ together with the nitrogen joining them as ring member form a morpholine, piperidine or pyrrolidine group;

$R^9$ and $R^{10}$ each denote, independently of one another, H, $C_{1-4}$-alkyl, $C_{2-4}$-alkenyl, $C_{2-4}$-alkinyl, $C_{3-8}$-cycloalkyl, —($C_{1, 2\ or\ 3}$-alkylene)-$C_{3-8}$-cycloalkyl, heterocycloalkyl, —($C_{1, 2\ or\ 3}$-alkylene)-heterocycloalkyl, aryl, heteroaryl, —($C_{1, 2\ or\ 3}$-alkylene)-aryl, or —($C_{1, 2\ or\ 3}$-alkylene)-heteroaryl;

$R^{21}$ and $R^{22}$, each denote, independently of one another, H, $C_{1-10}$-alkyl, $C_{2-10}$-alkenyl, $C_{2-10}$-alkinyl, $C_{3-8}$-cycloalkyl, —($C_{1, 2\ or\ 3}$-alkylene)-$C_{3-8}$-cycloalkyl, heterocycloalkyl, —($C_{1, 2\ or\ 3}$-alkylene)-heterocycloalkyl, aryl, heteroaryl, —($C_{1, 2\ or\ 3}$-alkylene)-aryl, or —($C_{1-2\ or\ 3}$-alkylene)-heteroaryl;

wherein the aforementioned $C_{1-10}$-alkyl, $C_{2-10}$-alkenyl and $C_{2-10}$-alkinyl groups each are linear or branched and can optionally be substituted with 1, 2, 3, 4 or 5 substituents independently selected from the group consisting of F, Cl, Br, —CN, COOH, COOC₁₋₄-alkyl, —OH, —SH, —O—C₁₋₂-alkyl, —S—C₁₋₂-alkyl, and —NH₂;

the aforementioned $C_{1-4}$-alkyl, $C_{2-4}$-alkenyl and $C_{2-4}$-alkinyl groups each are linear or branched and can optionally be substituted with 1, 2, 3, 4 or 5 substituents independently selected from the group consisting of F, Cl, Br, —CN, —OH, —OCH₃ and —NH₂;

the aforementioned $C_{3-8}$-cycloalkyl groups each may optionally be substituted with 1, 2, 3, 4 or 5 substituents independently selected from the group consisting of F, Cl, Br, —CN, —OH, —CH₃, —C₂H₅, —OCH₃, and —NH₂;

the aforementioned heterocycloalkyl groups each are 4-, 5-, 6- or 7-membered groups containing 1 or 2 heteroatoms independently selected from the group consisting of oxygen, sulfur and nitrogen as ring member(s), and can optionally be substituted with 1, 2, 3, 4 or 5 substituents independently selected from the group consisting of F, Cl, Br, —CN, —OH, —CH₃, —C₂H₅, —OCH₃ and —NH₂;

the aforementioned aryl groups each denote a phenyl, anthracenyl or naphthyl group, which optionally can be substituted with 1, 2, 3, 4 or 5 substituents independently selected from the group consisting of F, Cl, Br, —CF₃, —OCF₃, —SCF₃,

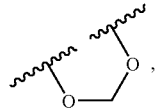

—NO₂, —C(=O)C₁₋₂-alkyl, cyclohexyl, —O(C=O)C₁₋₂-alkyl, —SF₅, —CN, —OH, methyl, ethyl, n-propyl, isopropyl, n-butyl, isobutyl, sec-butyl, tert.-butyl, methoxy, ethoxy, —NH₂, —N(CH₃)₂, —N(C₂H₅)₂, phenyl, benzyloxy, phenoxy, benzyl, thiophenyl (thienyl), furanyl and pyridinyl; and the aforementioned heteroaryl groups each denote a furanyl, thienyl (thiophenyl) or pyridinyl group and can optionally be substituted with 1, 2, 3, 4 or 5 substituents independently selected from the group consisting of F, Cl, Br, —CF₃, —OCF₃, —SCF₃, —SF₅, —CN, —OH, methyl, ethyl, n-propyl, isopropyl, n-butyl, isobutyl, sec-butyl, tert.-butyl, methoxy, ethoxy, —NH₂, —N(CH₃)₂, —N(C₂H₅)₂, phenyl, phenoxy, benzyl, thiophenyl (thienyl), furanyl and pyridinyl;

in the form of the racemate; in the form of the enantiomers, diastereomers, mixtures of the enantiomers or diastereomers, or of an individual enantiomer or diastereomer; in the form of the bases and/or salts of physiologically compatible acids.

Preferred are compounds in which $R^5$ denotes —C(=S)NR²¹R²². Also preferred are compounds in which $R^5$ denotes —(CHR⁶)ₙ—R²⁵. Furthermore, compounds are preferred in which n denotes 1. Particularly preferred are compounds in which $R^{21}$ denotes H, and $R^{22}$ denotes benzyl, phenyl, pyridyl, naphthyl or phenethyl, unsubstituted or monosubstituted or polysubstituted with methyl, ethyl, isopropyl, Cl, F, Br, NO₂, acetyl, CN, COOH, COOC₁₋₄-alkyl, methoxy, ethoxy, N(CH₃)₂, N(C₂H₅)₂,

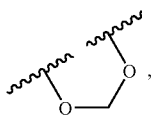

CF$_3$, or SCH$_3$; or R$^{22}$ denotes C$_{1-10}$-alkyl, branched or unbranched, saturated or unsaturated, unsubstituted or substituted with OCH$_3$, COOCH$_3$ or COOC$_2$H$_5$; C$_{3-6}$-cycloalkyl, in which the cycloalkyl group can be coupled via a CH$_2$ group; C$_{5-6}$-heterocycloalkyl, in which the heterocycloalkyl group can be coupled via a CH$_2$ group.

Most particularly preferred are compounds in which R$^{21}$ denotes H and R$^{22}$ denotes benzyl, phenyl, 2-methylphenyl, phenethyl, 2-isopropylphenyl, 2-chlorophenyl, 4-fluorobenzyl, 1-(4-fluorophenyl)ethyl, 4-chlorobenzyl, 4-chlorophenethyl, 4-nitrophenyl, 4-acetylphenyl, 3-carboxyphenyl, 3-methyl benzoate, 4-ethyl benzoate, 2,6-diethylphenyl, 3-chloro-4-methylphenyl, 2-methoxyethyl, 3-methoxypropyl, cyclopentyl, cyclohexyl, 3-pyridyl, 4-dimethylaminophenyl, 4-diethylaminophenyl, CH$_2$COOCH$_3$, CH(CH$_3$)COOC$_2$H$_5$, CH(CH$_3$)CH$_2$COOC$_2$H$_5$, cyclohexylmethyl, 4-ethoxyphenyl, 3,4-dimethoxyphenyl, 1-naphthyl, 3,4,5-trimethoxyphenyl, 2,3,4,5,6-pentafluorophenyl, benzodioxole, 4-fluorophenyl, methyl, ethyl, propyl, isopropyl, tert.-butyl, allyl, 2-methylprop-2-enyl, 2-nitrophenyl, 3-trifluoromethylphenyl, 2-trifluoromethylphenyl, 4-trifluormethylphenyl, cyclopropyl, 2-methylsulfanylphenyl, 3-methylsulfanylphenyl, 4-methylsulfanylphenyl, 3,5-dimethylphenyl, ethylmorpholine, ((4-propyl)cyclohexyl)phenyl, 4-bromo-2-trifluoromethylphenyl, n-octyl, n-nonanyl, tetrahydrofurylmethyl, 2-ethylphenyl, 4-cyanophenyl, 3-cyanophenyl, 2,6-diisopropylphenyl, n-pentyl, n-hexyl, sec-butyl, propylmorpholine, 5-chloro-2-methoxyphenyl, 4-chloro-3-trifluoromethylphenyl, 3-chlorophenyl, 1-phenylethyl, CH(CH$_3$)COOCH$_3$, 2-methoxyphenyl, 3-methoxyphenyl, 4-methoxyphenyl, CH$_2$CH$_2$COOC$_2$H$_5$, 2-methyl benzoate, 4-methyl benzoate, 2-ethyl benzoate, 2-fluorophenyl, 2-methoxy-5-chlorphenyl or 2,4-dimethoxyphenyl.

Also preferred are compounds in which R$^6$ denotes H. Likewise, compounds are preferred in which R$^6$ denotes CH$_3$.

Particularly preferred also are compounds in which R$^{25}$ denotes phenyl, anthracenyl, pyridyl, thienyl or furyl, in each case unsubstituted or monosubstituted or polysubstituted with CF$_3$, SCF$_3$, C$_{1-4}$-alkyl, Cl, NO$_2$, O-acetyl, OCH$_3$, F, O-phenyl, OCF$_3$, Br, O-benzyl, O-allyl, phenyl, I, CN or OH, preferably phenyl unsubstituted or substituted with the aforementioned groups.

Most particularly preferred are compounds in which R$^{25}$ denotes 4-trifluoromethylphenyl, 4-SCF$_3$-phenyl, 2-methylphenyl, phenyl, anthracenyl, 4-Cl-phenyl, 4-OCF$_3$-phenyl, 4-n-butylphenyl, 3(3-CF$_3$-phenoxy)-phenyl, 4-OCHF$_2$-phenyl, 3,5-dimethylphenyl, 3-bromo-4-methoxyphenyl, 4-benzyloxy-3,5-dimethylphenyl, 3-nitrophenyl, 3-methoxy-4-(acetylmethyl)-phenyl, 2,4,5-trimethoxyphenyl, 4-ethylphenyl, 3,4-dichlorophenyl, 2,3,5-trifluorophenyl, 4-phenoxyphenyl, 3-chloro-4-fluorophenyl, 3-benzyloxyphenyl, 3-bromo-4,5-dimethoxyphenyl, 3-fluoro-2-methylphenyl, 2-chloro-3-trifluoromethylphenyl, 3-chloro-2-fluoro-5-trifluoromethylphenyl, 2-fluoro-4-trifluoromethylphenyl, 4-(allyloxy)phenyl, 2-(benzyloxy)-4,5-dimethoxyphenyl, 2-phenylphenyl, 2,3,4-trifluorophenyl, 2-fluoro-5-trifluorophenyl, 4-methoxy-3-methylphenyl, 2-fluoro-3-chlorophenyl, 3,4-difluorophenyl, 2,6-dichlorophenyl, 3-iodophenyl, 3-iodo-4,5-dimethoxyphenyl, 2-cyanophenyl, 4-hydroxyphenyl, 3,4-dimethylphenyl or 3-OCF$_3$-phenyl.

Most preferred of all are compounds according to the invention selected from the group consisting of
benzo[d]isoxazol-3-yl-[1-(4-trifluoromethylphenyl)-ethyl]-amine,
benzo[d]isoxazol-3-yl-[1-(4-trifluoromethylsulfanylphenyl)-ethyl]-amine,
1-benzo[d]isoxazol-3-yl-3-benzyl-thiourea,
1-benzo[d]isoxazol-3-yl-3-phenyl-thiourea,
1-benzo[d]isoxazol-3-yl-3-o-tolyl-thiourea,
1-benzo[d]isoxazol-3-yl-3-phenethyl-thiourea,
1-benzo[d]isoxazol-3-yl-3-(2-isopropylphenyl)-thiourea,
1-benzo[d]isoxazol-3-yl-3-(2-chlorophenyl)-thiourea,
1-benzo[d]isoxazol-3-yl-3-(4-fluorobenzyl)-thiourea,
1-benzo[d]isoxazol-3-yl-3-[1-(4-fluorophenyl)-ethyl]-thiourea,
1-benzo[d]isoxazol-3-yl-3-(4-chlorobenzyl)-thiourea,
1-benzo[d]isoxazol-3-yl-3-[2-(4-chlorophenyl)-ethyl]-thiourea,
1-benzo[d]isoxazol-3-yl-3-(4-nitrophenyl)-thiourea,
1-(4-acetylphenyl)-3-benzo[d]isoxazol-3-yl-thiourea,
3-(3-benzo[d]isoxazol-3-yl-thioureido)-benzoic acid,
3-(3-benzo[d]isoxazol-3-yl-thioureido)-benzoic acid methyl ester,
4-(3-benzo[d]isoxazol-3-yl-thioureido)-benzoic acid ethyl ester,
1-benzo[d]isoxazol-3-yl-3-(2,6-diethylphenyl)-thiourea,
1-benzo[d]isoxazol-3-yl-3-(3-chloro-4-methylphenyl)-thiourea,
1-benzo[d]isoxazol-3-yl-3-(2-methoxyethyl)-thiourea,
1-benzo[d]isoxazol-3-yl-3-(3-methoxypropyl)-thiourea,
1-benzo[d]isoxazol-3-yl-3-cyclopentyl-thiourea,
1-benzo[d]isoxazol-3-yl-3-cyclohexyl-thiourea,
1-benzo[d]isoxazol-3-yl-3-pyridin-3-yl-thiourea,
1-benzo[d]isoxazol-3-yl-3-(4-dimethylaminophenyl)-thiourea,
1-benzo[d]isoxazol-3-yl-3-(4-diethylaminophenyl)-thiourea,
(3-benzo[d]isoxazol-3-yl-thioureido)-acetic acid methyl ester,
2-(3-benzo[d]isoxazol-3-yl-thioureido)-propionic acid ethyl ester,
3-(3-benzo[d]isoxazol-3-yl-thioureido)-butyric acid ethyl ester,
1-benzo[d]isoxazol-3-yl-3-cyclohexylmethyl-thiourea,
1-benzo[d]isoxazol-3-yl-3-(4-ethoxyphenyl)-thiourea,
1-benzo[d]isoxazol-3-yl-3-(3,4-dimethoxyphenyl)-thiourea,
1-benzo[d]isoxazol-3-yl-3-(3,4,5-trimethoxyphenyl)-thiourea,
1-benzo[d]isoxazol-3-yl-3-pentafluorophenyl-thiourea,
1-benzo[d]isoxazol-3-yl-3-naphthalen-1-yl-thiourea,
1-benzo[1,3]dioxol-5-ylmethyl-3-benzo[d]isoxazol-3-yl-thiourea,
1-benzo[d]isoxazol-3-yl-3-(4-fluorophenyl)-thiourea,
1-benzo[d]isoxazol-3-yl-3-methyl-thiourea,
1-benzo[d]isoxazol-3-yl-3-ethyl-thiourea,
1-benzo[d]isoxazol-3-yl-3-propyl-thiourea,
1-benzo[d]isoxazol-3-yl-3-isopropyl-thiourea,
1-benzo[d]isoxazol-3-yl-3-tert-butyl-thiourea,
1-allyl-3-benzo[d]isoxazol-3-yl-thiourea,
1-benzo[d]isoxazol-3-yl-3-(2-methylallyl)-thiourea,
1-benzo[d]isoxazol-3-yl-3-(2-nitrophenyl)-thiourea,
1-benzo[d]isoxazol-3-yl-3-(2-trifluoromethylphenyl)-thiourea, 1-benzo[d]isoxazol-3-yl-3-(3-trifluoromethylphenyl)-thiourea,
1-benzo[d]isoxazol-3-yl-3-(4-trifluoromethylphenyl)-thiourea,
1-benzo[d]isoxazol-3-yl-3-cyclopropyl-thiourea,
2-[3-(4-fluorobenzo[d]isoxazol-3-yl)-thioureido]-propionic acid methyl ester,
1-(4-chlorobenzo[d]isoxazol-3-yl)-3-o-tolyl-thiourea,
1-benzyl-3-(4-chlorobenzo[d]isoxazol-3-yl)-thiourea,
1-(4-chlorobenzo[d]isoxazol-3-yl)-3-(1-phenylethyl)-thiourea,
1-(4-dimethylaminobenzo[d]isoxazol-3-yl)-3-isobutyl-thiourea,
1-(4-dimethylaminobenzo[d]isoxazol-3-yl)-3-p-tolyl-thiourea,
1-(3-chlorophenyl)-3-(4-dimethylaminobenzo[d]isoxazol-3-yl)-thiourea,
1-(4-dimethylaminobenzo[d]isoxazol-3-yl)-3-(3-methoxyphenyl)-thiourea,
1-(4-dimethylaminobenzo[d]isoxazol-3-yl)-3-(2-methylsulfanylphenyl)-thiourea,
1-(4-dimethylaminobenzo[d]isoxazol-3-yl)-3-(3-methylsulfanyl-phenyl)-thiourea,
1-(4-dimethylaminobenzo[d]isoxazol-3-yl)-3-(4-methylsulfanylphenyl)-thiourea,
1-(4-dimethylamino-benzo[d]isoxazol-3-yl)-3-(2-methoxyphenyl)-thiourea,
1-(4-dimethylaminobenzo[d]isoxazol-3-yl)-3-(4-methoxyphenyl)-thiourea,
1-(4-dimethylaminobenzo[d]isoxazol-3-yl)-3-(3,5-dimethylphenyl)-thiourea,
1-benzyl-3-(4-dimethylaminobenzo[d]isoxazol-3-yl)-thiourea,
1-(4-dimethylaminobenzo[d]isoxazol-3-yl)-3-(3-methoxypropyl)-thiourea,
3-[3-(4-dimethylamino-benzo[d]isoxazol-3-yl)-thioureido]-propionic acid ethyl ester,
2-[3-(4-dimethylaminobenzo[d]isoxazol-3-yl)-thioureido]-propionic acid ethyl ester,
3-[3-(4-dimethylaminobenzo[d]isoxazol-3-yl)-thioureido]-butyric acid ethyl ester,
3-[3-(4-dimethylaminobenzo[d]isoxazol-3-yl)-thioureido]-benzoic acid,
1-(4-dimethylaminobenzo[d]isoxazol-3-yl)-3-(4-ethoxyphenyl)-thiourea,
2-[3-(4-dimethylaminobenzo[d]isoxazol-3-yl)-thioureido]-benzoic acid methyl ester,
3-[3-(4-dimethylaminobenzo[d]isoxazol-3-yl)-thioureido]-benzoic acid methyl ester,
4-[3-(4-dimethylaminobenzo[d]isoxazol-3-yl)-thioureido]-benzoic acid methyl ester,
2-[3-(4-dimethylaminobenzo[d]isoxazol-3-yl)-thioureido]-benzoic acid ethyl ester,
4-[3-(4-dimethylamino-benzo[d]isoxazol-3-yl)-thioureido]-benzoic acid ethyl ester,
1-(4-acetylphenyl)-3-(4-dimethylaminobenzo[d]isoxazol-3-yl)-thiourea,
1-(2-chlorophenyl)-3-(4-methoxybenzo[d]isoxazol-3-yl)-thiourea,
1-(4-diethylaminophenyl)-3-(4-methoxy-benzo[d]isoxazol-3-yl)-thiourea,
1-(4-methoxybenzo[d]isoxazol-3-yl)-3-(2-morpholin-4-yl-ethyl)-thiourea,
2-(3-[4-(2,2,2-trifluoroethoxy)-benzo[d]isoxazol-3-yl]-thioureido)-propionic acid methyl ester,
1-benzo[1,3]dioxol-5-ylmethyl-3-[4-(2,2,2-trifluoroethoxy)-benzo[d]isoxazol-3-yl]-thiourea,
1-[4-(4-propylcyclohexyl)-phenyl]-3-[4-(2,2,2-trifluoroethoxy)-benzo[d]isoxazol-3-yl]thiourea,
1-(4-bromo-2-trifluoromethylphenyl)-3-[4-(2,2,2-trifluoroethoxy)-benzo[d]isoxazol-3-yl]thiourea,
1-(4-methoxyphenyl)-3-[4-(2,2,2-trifluoroethoxy)-benzo[d]isoxazol-3-yl]-thiourea,
3-(3-[4-(2,2,2-trifluoroethoxy)-benzo[d]isoxazol-3-yl]-thioureido)-propionic acid ethyl ester
1-[4-(4-methylbenzyloxy)-benzo[d]isoxazol-3-yl)-3-octyl-thiourea,
1-[4-(4-methylbenzyloxy)-benzo[d]isoxazol-3-yl)-3-nonyl-thiourea
1-cyclopropyl-3-[4-(4-methylbenzyloxy)-benzo[d]isoxazol-3-yl]-thiourea,
1-cyclopentyl-3-[4-(4-methylbenzyloxy)-benzo[d)isoxazol-3-yl-thiourea,
1-cyclohexyl-3-[4-(4-methylbenzyloxy)-benzo[d]isoxazol-3-yl]-thiourea,
1-cyclohexylmethyl-3-[4-(4-methylbenzyloxy)-benzo[d]isoxazol-3-yl)-thiourea,
1-(4-dimethylaminophenyl)-3-[4-(2,2,2-trifluoroethoxy)-benzo[d]isoxazol-3-yl]-thiourea,
1-allyl-3-(5-methylbenzo[d]isoxazol-3-yl)-thiourea,
[3-(5-methylbenzo[d]isoxazol-3-yl)-thioureido]-acetic acid methyl ester,
1-(2-isopropylphenyl)-3-(5-methylbenzo[d]isoxazol-3-yl)-thiourea,
1-(5-methylbenzo[d]isoxazol-3-yl)-3-(4-trifluoromethylphenyl)-thiourea,
2-[3-(5-fluorobenzo[d]isoxazol-3-yl)-thioureido]-propionic acid methyl ester,
1-(5-fluorobenzo[d]isoxazol-3-yl)-3-(tetrahydrofuran-2-ylmethyl)-thiourea,
1-(5-bromobenzo[d]isoxazol-3-yl)-3-(2-fluorophenyl)-thiourea,
1-(5-bromobenzo[d]isoxazol-3-yl)-3-(2-ethylphenyl)-thiourea,
1-(6-chlorobenzo[d]isoxazol-3-yl)-3-(4-fluorophenyl)-thiourea,
1-(6-chlorobenzo[d]isoxazol-3-yl)-3-(2-fluorophenyl)-thiourea,
1-(6-chlorobenzo[d]isoxazol-3-yl)-3-cyclopentyl-thiourea,
1-(6-chlorobenzo[d]isoxazol-3-yl)-3-(4-cyanophenyl)-thiourea,
3-[3-(6-chlorobenzo[d]isoxazol-3-yl)-thioureido]-benzoic acid,
1-(6-chlorobenzo[d]isoxazol-3-yl)-3-(4-methoxyphenyl)-thiourea,
1-(6-chlorobenzo[d]isoxazol-3-yl)-3-(3-methoxyphenyl)-thiourea,
1-(6-bromobenzo[d]isoxazol-3-yl)-3-(3,4-dimethoxyphenyl)-thiourea,
1-(6-bromobenzo[d]isoxazol-3-yl)-3-naphthalen-1-yl-thiourea,
1-benzo[1,3]dioxol-5-ylmethyl-3-(6-bromobenzo(diisoxazol-3-yl)-thiourea,
1-(6-fluorobenzo[d]isoxazol-3-yl)-3-(2-methylsulfanylphenyl)-thiourea,
1-(3-cyanophenyl)-3-(6-fluorobenzo[d]isoxazol-3-yl)-thiourea,
1-(2-chloro-6-methylphenyl)-3-(6-fluorobenzo[d]isoxazol-3-yl)-thiourea,
1-(2,6-diisopropylphenyl)-3-(6-fluorobenzo[d]isoxazol-3-yl)-thiourea,
1-(7-fluorobenzo[d]isoxazol-3-yl)-3-methyl-thiourea,
1-ethyl-3-(7-fluorobenzo[d]isoxazol-3-yl)-thiourea,
1-(7-fluorobenzo[d]isoxazol-3-yl)-3-propyl-thiourea, 1-(7-fluorobenzo[d]isoxazol-3-yl)-3-pentyl-thiourea,
1-(7-fluorobenzo[d]isoxazol-3-yl)-3-hexyl-thiourea,
1-(7-fluorobenzo[d]isoxazol-3-yl)-3-octyl-thiourea,
1-(7-fluorobenzo[d]isoxazol-3-yl)-3-nonyl-thiourea,
1-(7-fluorobenzo[d]isoxazol-3-yl)-3-isobutyl-thiourea,
1-allyl-3-(7-fluorobenzol[d]isoxazol-3-yl)-thiourea,
1-(7-fluorobenzo[d]isoxazol-3-yl)-3-p-tolyl-thiourea,
1-(5-bromobenzo[d]isoxazol-3-yl)-3-(4-dimethylaminophenyl)-thiourea,
1-(7-fluorobenzo[d]isoxazol-3-yl)-3-(2-morpholin-4-yl-ethyl)-thiourea,
1-(7-fluorobenzo[d]isoxazol-3-yl)-3-(3-morpholin-4-yl-propyl)-thiourea,
1-(4-methoxybenzo[d]isoxazol-3-yl)-3-(1-phenylethyl)-thiourea,
1-(4-chlorobenzyl)-3-(4-methoxybenzo[d]isoxazol-3-yl)-thiourea,
1-(4-methoxybenzo[d]isoxazol-3-yl)-3-(2-methoxyphenyl)-thiourea,
1-(5-bromobenzo[d]isoxazol-3-yl)-3-(4-dimethylaminophenyl)-thiourea,
1-(5-chloro-2-methoxyphenyl)-3-(4-methoxybenzo[d]isoxazol-3-yl)-thiourea,
1-(4-chloro-3-trifluoromethylphenyl)-3-(4-methoxy-benzo[d]isoxazol-3-yl)-thiourea,
1-(2,4-dimethoxyphenyl)-3-(4-methoxybenzo[d]isoxazol-3-yl)-thiourea,
1-[4-(2,2,2-trifluoroethoxy)-benzo[d]isoxazol-3-yl]-3-(3,4,5-trimethoxyphenyl)-thiourea,
benzo[d]isoxazol-3-yl-(3-methylbutyl)-amine,
(5-fluorobenzo[d]isoxazol-3-yl)-(2-methylbenzyl)amine,
N4,N4-dimethyl-N3-(3-phenylpropyl)-benzo[d]isoxazol-3,4-diamine,
N3-butyl-N4,N4-dimethylbenzo[d]isoxazol-3,4-diamine,
anthracene-9-ylmethyl-(4-methoxybenzo[d]isoxazol-3-yl)-amine,
(4-chlorobenzyl)-(4-methoxybenzo[d]isoxazol-3-yl)-amine,
(6-fluorobenzo[d]isoxazol-3-yl)-(3-nitrobenzyl)-amine,
acetic acid-4-[(6-chlorobenzo[d]isoxazol-3-ylamino)-methyl]-2-methoxyphenyl ester,
acetic acid-4-[(6-bromobenzo[d]isoxazol-3-ylamino)methyl]-2-methoxyphenyl ester,
benzo[d]isoxazol-3-yl-(3,4-dichlorobenzyl)amine,
benzo[d]isoxazol-3-yl-(2,4,5-trimethoxybenzyl)amine,
benzo[d]isoxazol-3-yl-(4-ethylbenzyl)-amine,
(6-chlorobenzo[d]isoxazol-3-yl)-(3,4-dichlorobenzyl)-amine,
benzo[d]isoxazol-3-yl-(2,3,5-trifluorobenzyl)-amine,
(6-chlorobenzo[d]isoxazol-3-yl)-(4-phenoxybenzyl)-amine,
(3-chloro-4-fluorobenzyl)-(7-fluorobenzo[d]isoxazol-3-yl)-amine,
benzo[d]isoxazol-3-yl-(4-trifluoromethylbenzyl)-amine,
(7-fluorobenzo[d]isoxazol-3-yl)-(2-methylpentyl)-amine,
N4,N4-dimethyl-N3-(2,3,4-trifluorobenzyl)-benzo[d]isoxazol-3,4-diamine,
N3-(2-fluoro-5-trifluoromethylbenzyl)-N4,N4-dimethyl-benzo[d]isoxazole-3,4-diamine,
N3-(4-methoxy-3-methylbenzyl)-benzo[d]isoxazole-3,4-diamine,
N3-(4-methoxy-3-methylbenzyl)-benzo[d]isoxazole-3,4-diamine,
benzo[d]isoxazol-3-yl-(4-trifluoromethoxybenzyl)-amine,
(5-fluorobenzo[d]isoxazol-3-yl)-(4-trifluoromethoxybenzyl)-amine,
benzo[d]isoxazol-3-yl-(4-trifluoromethylsulfanylbenzyl)-amine,
(4-butylbenzyl)-(6-chlorobenzo[d]isoxazol-3-yl)-amine,
(5-fluorobenzo[d]isoxazol-3-yl)-(4-trifluoromethylsulfanylbenzyl)-amine,
benzo[d]isoxazol-3-yl-(2-fluoro-4-trifluoromethylbenzyl)-amine,
(7-fluorobenzo[d]isoxazol-3-yl)-(4-trifluoromethoxybenzyl)-amine,
(7-fluorobenzo[d]isoxazol-3-yl)-[3-(3-trifluoromethylphenoxy)-benzyl]-amine,
(4-difluoromethoxybenzyl)-(4-methoxybenzol[d]isoxazol-3-yl)-amine,
(3,5-dimethylbenzyl)-(7-fluorobenzo[d]isoxazol-3-yl)-amine,
(3-bromo-4-methoxybenzyl)-(6-fluorobenzo[d]isoxazol-3-yl)-amine,
(3,5-dimethylbenzyl)-(6-fluorobenzo[d]isoxazol-3-yl)-amine,
(4-benzyloxy-3,5-dimethylbenzyl)-(6-fluorobenzo[d]isoxazol-3-yl)-amine,
(4-butylbenzyl)-(6-fluorobenzo[d]isoxazol-3-yl)-amine,
(6-fluorobenzo[d]isoxazol-3-yl)-(4-trifluoromethylsulfanylbenzyl)-amine,
(3-benzyloxybenzyl)-(6-fluorobenzo[d]isoxazol-3-yl)-amine,
N3-(3,5-dimethylbenzyl)-benzo[d]isoxazole-3,4-diamine,
N3-(4-butylbenzyl)-benzo[d]isoxazole-3,4-diamine,
(5-bromobenzo[d]isoxazol-3-yl)-(4-trifluoromethylsulfanyl-benzyl)-amine,
(3-bromo-4,5-dimethoxybenzyl)-(7-fluorobenzo[d]isaxazole-3-yl)-amine,
(7-fluorobenzo[d]isoxazol-3-yl)-(2-fluoro-4-trifluoromethylbenzyl)-amine,
N3-(3-fluoro-2-methylbenzyl)-N4,N4-dimethylbenzo[d]isoxazole-3,4-diamine,
N3-(2-chloro-3-trifluoromethylbenzyl)-N4,N4-dimethylbenzo[d]isoxazole-3,4-diamine,
N3-(3-chloro-2-fluoro-5-trifluoromethyl-benzyl)-N4,N4-dimethyl-benzo[d]isoxazole-3,4-diamine,
(6-fluorobenzo[d]isoxazol-3-yl)-(2-fluoro-4-trifluoromethyl-benzyl)-amine,
(4-allyloxybenzyl)-(6-fluorobenzo[d]isoxazol-3-yl)-amine
Benzo[d]isoxazol-3-yl-(2-benzyloxy-4,5-dimethoxybenzyl)-amine,
(2-benzyloxy-4,5-dimethoxybenzyl)-(6-chlorobenzo[d]isoxazol-3-yl)-amine,
N3-(2-benzyloxy-4,5-dimethoxybenzyl)-N4,N4-dimethyl-benzo[d]isoxazole-3,4-diamine,
N3-biphenyl-2-ylmethyl-N4,N4-dimethylbenzo[d]isoxazole-3,4-diamine,
(6-fluorobenzo[d]isoxazol-3-yl)-(3-iodobenzyl)-amine,
(2-benzyloxy-4,5-dimethoxybenzyl)-(4-methoxy-benzo[d]isoxazol-3-yl)-amine,
(4-fluorobenzo[d]isoxazol-3-yl)-(3-iodo-4,5-dimethoxybenzyl)-amine,
2-[(5-methylbenzo[d]isoxazol-3-ylamino)-methyl)-benzonitrile,
butyl-[4-(2,2,2-trifluoroethoxy)-benzo[d]isoxazol-3-yl]-amine,
(3-bromo-4,5-dimethoxybenzyl)-(5-methylbenzo[d]isoxazol-3-yl)-amine,
4-[(4-chlorobenzo[d]isoxazol-3-ylamino)-methyl]-phenol,
(6-chlorobenzo[d]isoxazol-3-yl)-(3,4-dimethylbenzyl)-amine,
(4-chlorobenzo[d]isoxazol-3-yl)-(3-chloro-2-fluorobenzyl)-amine,
(3,4-difluorobenzyl)-(5-fluorobenzo[d]isoxazol-3-yl)-amine, (6-bromobenzo[d]isoxazol-3-yl)-2,6-dichlorobenzyl)-amine, and
(7-fluorobenzo[d]isoxazol-3-yl)-(3-trifluoromethoxybenzyl)-amine, as well as in each case their corresponding salts, in particular their hydrochloride addition salts, and optionally in each case their corresponding solvates.

The present invention also provides a process for the production of the substituted benzo(d)isoxazol-3-yl amine compounds according to the invention, in accordance with which an optionally substituted 2-fluorobenzonitrile compound corresponding to formula II,

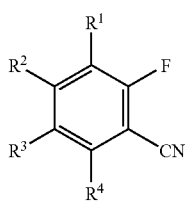

II wherein the groups $R^1$, $R^2$, $R^3$ and $R^4$ have the aforementioned meanings, is reacted in a reaction medium, preferably selected from the group consisting of diethyl ether, tetrahydrofuran, acetonitrile, dimethyl sulfoxide, dimethylformamide and dichloromethane, in the presence of a base, preferably in the presence of at least one alkali metal alcoholate salt, particularly preferably in the presence of an alkali metal alcoholate salt selected from the group consisting of potassium methanolate, sodium methanolate, potassium tert.-butylate and sodium tert.-butylate, with acetohydroxamic acid of the formula III

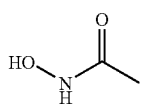

III preferably at temperatures from 20° C. to 100° C., to form a compound corresponding to formula I

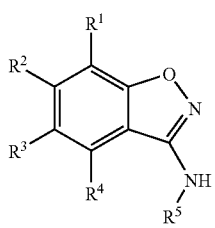

I wherein the groups $R^1$-$R^4$ have the aforementioned meanings and the group $R^5$ denotes a hydrogen group, and this compound is optionally purified and/or optionally isolated, following which this compound is optionally reacted in a reaction medium, preferably selected from the group consisting of acetonitrile, toluene, dimethylformamide, benzene, ethanol, methanol and corresponding mixtures, with at least one isothiocyanate corresponding to formula S=C=N—$R^{22}$, wherein $R^{22}$ has the aforementioned meaning, optionally in the presence of a base, preferably in the presence of at least one base selected from the group consisting of triethylamine, 4,4-dimethylaminopyridine and diisopropylethylamine, to form at least one compound corresponding to formula I, wherein $R^1$, $R^2$, $R^3$, $R^4$ have the aforementioned meanings and $R^5$ denotes —C(=S)—$NR^{21}R^{22}$, wherein $R^{22}$ has the aforementioned meaning and $R^{21}$ denotes a hydrogen group, and this compound is optionally purified and/or optionally isolated, and optionally at least one compound corresponding to formula I, wherein $R^1$, $R^2$, $R^3$, $R^4$ have the aforementioned meanings, $R^5$ denotes —C(=S)—$NR^{21}R^{22}$, wherein $R^{22}$ has the aforementioned meaning and $R^{21}$ denotes a hydrogen group, is reacted in a reaction medium, preferably selected from the group consisting of acetonitrile, toluene, dimethylformamide, benzene, ethanol, methanol and corresponding mixtures, in the presence of at least one base, preferably in the presence of at least one metal hydride salt or a metal alcoholate salt, particularly preferably in the presence of a metal hydride salt or a metal alcoholate salt selected from the group consisting of sodium hydride, potassium hydride, potassium tert.-butanolate, sodium tert.-butanolate, potassium methanolate, sodium methanolate, sodium ethanolate and potassium ethanolate, with at least one compound corresponding to formula LG-$R^{21}$, wherein LG denotes a leaving group, preferably a halogen atom, particularly preferably a chlorine atom, and $R^{21}$ has the aforementioned meaning with the exception of hydrogen, to form at least one compound corresponding to formula I, which is optionally purified and/or optionally isolated, or optionally at least one compound corresponding to formula I, wherein $R^1$, $R^2$, $R^3$, $R^4$ have the aforementioned meanings and $R^5$ denotes H, is reacted in a reaction medium, preferably selected from the group consisting of acetonitrile, toluene, dimethylformamide, benzene, ethanol, methanol, DCM, trifluoroacetic acid and corresponding mixtures, in the presence of at least one base, preferably in the presence of at least one metal hydride salt or a metal alcoholate salt or triethylsilane, particularly preferably in the presence of triethylsilane, a metal hydride salt or a metal alcoholate salt selected from the group consisting of sodium hydride, potassium hydride, potassium tert.-butanolate, sodium tert.-butanolate, potassium methanolate, sodium methanolate, sodium ethanolate and potassium ethanolate, with at least one compound corresponding to formula $R^{30}C(=O)H$ or $R^6C(O)R^{25}$, wherein $R^6$ and $R^{25}$ have the aforementioned meanings and $R^{30}$ denotes a linear or branched, saturated or unsaturated, unsubstituted or mono- or polysubstituted aliphatic group; or denotes an unsubstituted or mono- or polysubstituted aryl or heteroaryl group, which can be condensed with a monocyclic or polycyclic ring system; or denotes an unsubstituted or mono- or polysubstituted aryl or heteroaryl group, which can be condensed with a monocyclic or polycyclic ring system and is bonded via a linear or branched alkylene group, to form at least one compound corresponding to formula I, this compound being optionally purified and/or optionally isolated.

If the group $R^{30}$ is defined in a specific compound, this means that in this case in structures corresponding to formula I, $R^5$ denotes $CH_2R^{30}$.

The chemicals and reactants used in the aforedescribed reactions are commercially obtainable or can in each case be prepared by conventional methods known to the person skilled in the art.

The aforedescribed reactions can additionally each be carried out under conventional conditions known to those skilled in the art, for example as regards pressure, temperature, protective gas atmosphere or sequence of addition of the components. If necessary the optimal reaction procedure for the respective conditions can be determined by a person skilled in the art by simple preliminary experiments.

The intermediate products and end products obtained by the aforedescribed reactions can in each case, if desired and/ or if necessary, be purified and/or isolated by conventional methods known to those skilled in the art. Suitable purification processes include, for example, extraction processes and chromatographic processes such as column chromatography or preparative chromatography and also HPLC.

All the process steps described above as well as in each case also the purification and/or isolation of the intermediate products or end products can be carried out partially or completely under an inert gas atmosphere, preferably under a nitrogen atmosphere or argon atmosphere.

The substituted benzo(d)isoxazol-3-yl amine compounds according to the invention can be isolated in the form of their free bases, their free acids, and also in each case in the form of corresponding salts, in particular physiologically compatible salts.

The free bases of the respective substituted benzo(d)isoxazol-3-yl amine compounds according to the invention can be converted into the corresponding salts, preferably physiologically compatible salts, for example by reaction with an inorganic or organic acid, preferably with hydrochloric acid, hydrobromic acid, sulfuric acid, phosphoric acid, methanesulfonic acid, p-toluenesulfonic acid, carbonic acid, formic acid, acetic acid, oxalic acid, maleic acid, malic acid, succinic acid, tartaric acid, mandelic acid, fumaric acid, lactic acid, citric acid, glutamic acid or aspartic acid.

The free bases of the respective substituted benzo(d)isoxazol-3-yl amine compounds according to the invention can similarly be converted with the free acid or a salt of a sugar substitute, such as for example saccharine, cyclamate or acesulfam, into the corresponding physiologically compatible salts.

The free acids of the substituted benzo(d)isoxazol-3-yl amine compounds according to the invention can correspondingly be converted by reaction with a suitable base into the corresponding physiologically compatible salts. The alkali metal salts, alkaline earth metal salts or ammonium salts $[NH_xR_{4-x}]^+$, where x=0, 1, 2, 3 or 4 and R denotes a linear or branched $C_{1-4}$ alkyl group, may be mentioned by way of example.

The substituted benzo(d)isoxazol-3-yl amine compounds according to the invention, in the same way as the corresponding acids, the corresponding bases or salts of these compounds, can optionally be obtained also in the form of their solvates, preferably in the form of their hydrates, by methods known to the person skilled in the art.

If the substituted benzo(d)isoxazol-3-yl amine compounds according to the invention are after their preparation obtained in the form of a mixture of their stereoisomers, preferably in the form of their racemates or other mixtures of their various enantiomers and/or diastereomers, these can be separated and optionally isolated by methods known to the person skilled in the art. Examples of suitable known separation processes include chromatographic separation processes, in particular liquid chromatography processes under normal pressure or under elevated pressure, preferably MPLC and HPLC processes, as well as fractional crystallisation processes. In this way individual enantiomers, for example diastereomeric salts formed by means of HPLC on a chiral stationary phase or by means of crystallisation with chiral acids, for example (+)-tartaric acid, (−)-tartaric acid or (+)-10-camphorsulfonic acid, can be separated from one another.

The substituted benzo(d)isoxazol-3-yl amine compounds according to the invention as well as in each case the corresponding acids, bases, salts and solvates are suitable as pharmaceutical active substances in medicaments. The present invention accordingly also provides a pharmaceutical composition or medicament containing at least one substituted benzo(d)isoxazol-3-yl amine compound according to the invention as well as optionally one or more pharmaceutically compatible auxiliary substances. These medicaments according to the invention are suitable for influencing KCNQ2/3 channels and exert in particular an agonistic action.

The pharmaceutical compositions according to the invention are suitable for the treatment or inhibition of disorders or conditions which are mediated at least in part via KCNQ2/3 channels. Examples of conditions which can be treated or inhibited using compositions comprising the compounds according to the present invention include pain, particularly pain selected from the group consisting of acute pain, chronic pain, neuropathic pain, muscular pain and inflammatory pain; migraine; epilepsy; anxiety states and urinary incontinence. The pharmaceutical compositions according to the invention are particularly suitable for the treatment of pain, especially chronic pain, neuropathic pain, inflammatory pain and muscular pain.

The present invention also provides for the use of at least one substituted benzo(d)isoxazol-3-yl amine compound according to the invention as well as optionally one or more pharmaceutically compatible auxiliary substances, for the production of a medicament for the treatment of disorders or conditions that are mediated at least in part by KCNQ2/3 channels. It is preferred to use at least one substituted benzo (d)isoxazol-3-yl amine compound according to the invention as well as optionally one or more pharmaceutically compatible auxiliary substances for the production of a medicament for the treatment of pain, preferably pain selected from the group consisting of acute pain, chronic pain, neuropathic pain, muscular pain and inflammatory pain; migraine; epilepsy; anxiety states and urinary incontinence. It is particularly preferred to use at least one substituted benzo(d)isoxazol-3-yl amine compound according to the invention and also optionally one or more pharmaceutically compatible auxiliary substances, for the production of a medicament for the treatment of pain, especially chronic pain, neuropathic pain, inflammatory pain and muscular pain.

The pharmaceutical composition according to the invention can be present in the form of a liquid, semi-solid or solid medicament form, for example in the form of injection solutions, drops, juices, syrups, sprays, suspensions, tablets, patches, capsules, plasters, suppositories, ointments, creams, lotions, gels, emulsions, aerosols or in multiparticulate form, for example in the form of pellets or granules, optionally compressed into tablet form, packaged in capsules or suspended in a liquid, and can also be administered as such. Besides at least one substituted benzo(d)isoxazol-3-yl amine compound according to the invention, the pharmaceutical composition according to the invention usually contains further physiologically compatible pharmaceutical auxiliary substances, which can preferably be selected from the group consisting of carrier materials, fillers, solvents, diluents, surface-active substances, coloring agents, preservatives, disintegrants, pharmaceutical lubricants, ointments, aroma substances and binders. The choice of the physiologically compatible auxiliary substances as well as the amounts thereof to be employed depends on whether the medicament is to be administered orally, subcutaneously, parenterally, intravenously, intraperitoneally, intradermally, intramuscularly, intranasally, buccally, rectally or topically, for example to infections on the skin, mucus membranes and eyes.

For oral administration, preparations in the form of tablets, coated pills, capsules, pellets, drops, juices and syrups are preferred, while for parenteral, topical and inhalative application, solutions, suspensions, easily reconstitutable dry preparations and also sprays are preferred. The substituted benzo(d)isoxazol-3-yl amine compounds used in the pharmaceutical composition according to the invention also can be present as suitable percutaneous application preparations, in a depot form, in dissolved form or in a plaster, optionally with the addition of agents promoting penetration of the skin. Orally or percutaneously usable preparation forms can also release the respective substituted benzo(d)isoxazol-3-yl amine compound according to the invention in a delayed manner.

Pharmaceutical compositions according to the invention are produced using conventional means, apparatus, equipment, methods and processes known in the art, such as are described for example in "Remingtons Pharmaceutical Sciences", Editor A. R. Gennaro, 17$^{th}$ Edition, Mack Publishing Company, Easton, Pa., 1985, in particular in Part 8, Chapters 76 to 93, which are hereby incorporated by reference as part of the disclosure herein.

The amount of the respective substituted benzo(d)isoxazol-3-yl amine compound according to the invention to be administered to the patient can vary, and depends for example on the weight or age of the patient as well as on the manner of administration, the medical indication and the severity of the disease. Normally 0.005 to 100 mg/kg, preferably 0.05 to 75 mg/kg body weight of the patient of at least one such compound according to the invention is administered.

The invention is described in further detail hereinafter with reference to some examples. These descriptions are given simply by way of example and do not restrict the general scope of the invention.

EXAMPLES

In the examples, the yields of the prepared compounds are not optimized, and all temperatures are uncorrected. The chemicals and solvents used were obtained commercially from the usual suppliers (Acros, Avocado, Aldrich, Bachem, Fluka, Lancaster, Maybridge, Merck, Sigman TCl, etc.) or were synthesised by methods known to persons skilled in the art. Silica gel 60 (0.040-0.063 mm) from E. Merck, Darmstadt, was used as stationary phase for the column chromatography. The thin-layer chromatographic investigations were carried out with HPTLC precoated plates, silica gel 60 F 254, from E. Merck, Darmstadt. The mixing ratios of solvents, chromatography solvents or for chromatographic investigations are always given in volume/volume. The analysis was carried out by HPLC-MS or NMR. In most cases a purity of >80% was achieved. The following abbreviations are used in the examples:

| aq. | aqueous |
| APCI | atmospheric pressure chemical ionisation |
| Equiv. | Quantitative equivalents |
| DCM | Dichloromethane |
| DMF | Dimethylformamide |
| DMSO | Dimethyl sulfoxide |
| EtOAc | Ethyl acetate |

| | -continued |
| --- | --- |
| sat. | saturated |
| h | hours |
| min | minutes |
| NMR | nuclear magnetic resonance spectroscopy |
| RT | room temperature |

General Instructions for the Preparation of the Benzisoxazole Skeleton Structure:

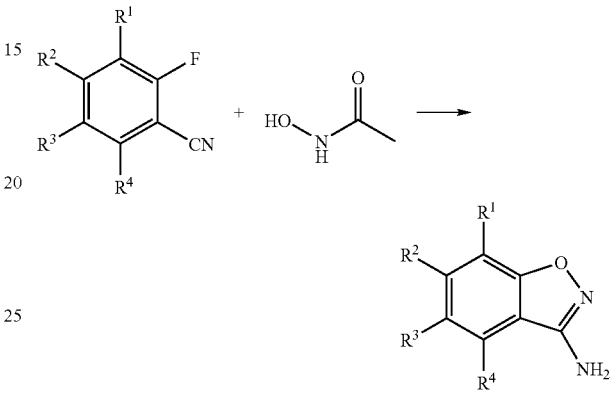

The skeleton structure of the benzisoxazoles according to the invention was prepared according to the instructions of Palermo (M. G. Palermo, Tetrahedron Lett. 1996; 37; 17; 2885-2886), the entire disclosure of which is hereby incorporated by reference as part of the disclosure herein. As a variant of the aforementioned instructions, the purification of the benzisoxasole compounds was carried out in some cases by precipitation of the corresponding HCL salt.

Procedure:

Acetohydroxamic acid (1.1 equiv.) in DMF (1.45 ml/mmole of acetohydroxamic acid) was suspended in a three-necked flask. Potassium tert.-butylate (1.1 equiv.) was added under an inert gas. The reaction mixture was stirred for 30 minutes at room temperature and the optionally substituted 2-fluorobenzonitrile (1 equiv.) was then added. The reaction mixture was heated to 50° C. and stirred for one hour at this temperature. After cooling, the reaction mixture was added to a mixture (1.8 ml/mmole of acetohydroxamic acid) of equal parts by volume of saturated NaCl solution and ethyl acetate and stirred well for 30 minutes. The phases were separated and the aqueous phase was extracted three times with ethyl acetate (each time with 0.8 ml/mmole of acetohydroxamic acid). The organic phases were combined and washed three times with saturated NaCl solution (each time with 0.8 ml/mmole of acetohydroxamic acid) and then dried over magnesium sulfate. The magnesium sulfate was filtered out, and the filtrate was concentrated, initially on a rotary evaporator and then using an oil pump.

For further purification the obtained hydrochloride was advantageously in some cases precipitated. For this purpose the residue was dissolved in methyl ethyl ketone (8.7 ml/g of residue). After adding water (0.1 ml/g of residue), trimethylchlorosilane (0.7 ml/g of residue) was slowly added dropwise while stirring and cooling with iced water. The flask was kept overnight in a refrigerator, and the resultant precipitate was filtered out and dried in a desiccator using phosphorus pentoxide as drying agent.

The following intermediate compounds were prepared in this way:
A
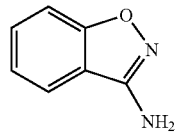
B
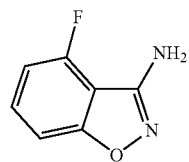
C
D
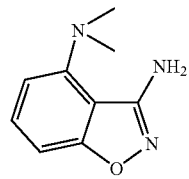
E
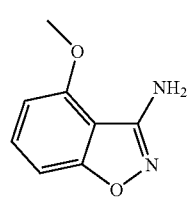
F
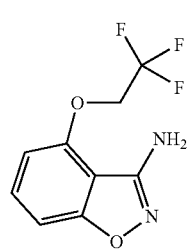
G
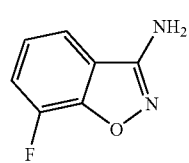
H
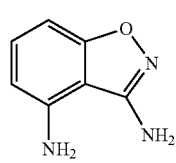
I
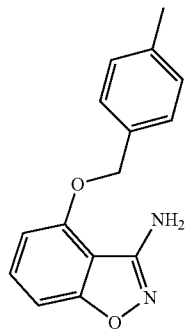
J
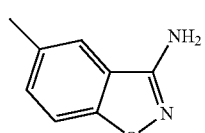
K
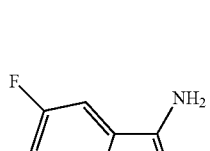
L
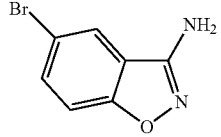
M
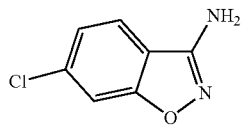
N
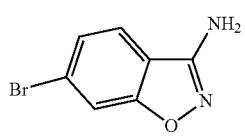
O
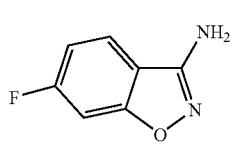

-continued

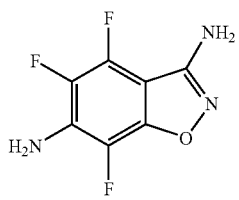

General Instructions for the Reductive Amination of the Amino-Substituted Benzisoxazole Skeleton Structure for the Preparation of α-Alkyl-Substituted Benzisoxazolamines:

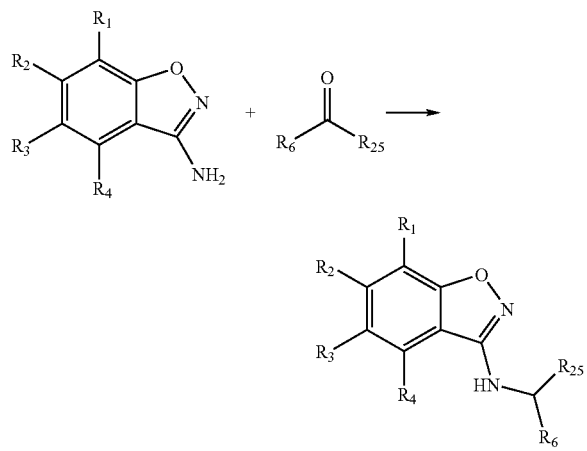

Procedure:

The respective benzisoxazole (4.55 mmole, 1 equiv.) was dissolved in DCM (11 ml), the corresponding alkyl phenyl ketone (4.55 mmole, 1 equiv.) was added, and the mixture was stirred for 1 hour at room temperature under an inert gas. Triethylsilane (4.5 mmole, 1 equiv.) and trifluoroacetic acid (13.65 mmole, 3 equivs.) were then added dropwise under inert conditions and the reaction mixture was stirred under reflux for 4-12 hours. After cooling, the mixture was adjusted to pH 8-9 with sat. $NaHCO_3$ solution and the aqueous phase was extracted 4 times with DCM. The combined organic phases were dried over $MgSO_4$ and concentrated by evaporation. The resulting crude product was purified by flash chromatography (diethyl ether/hexane).

The following alkyl phenyl ketones were reacted according to this procedure:

| No. | Alkyl phenyl ketone |
|---|---|
| Z1 | 4-(trifluoromethyl)acetophenone |
| Z2 | 4-(trifluoromethylsulfanyl)acetophenone |

The compounds of the following examples were synthesised according to the foregoing procedures. The identifying numbers of the educts employed are given in the Table.

Employed Educts

| Example | Benzisoxazole | Alkyl phenyl ketone | Molecular weight | Identified by: (Purity) | Name |
|---|---|---|---|---|---|
| 1 | A | Z1 | 306.286992 | NMR | Benzo[d]isoxazol-3-yl-[1-(4-trifluoro-methylphenyl)-ethyl]-amine |
| 2 | A | Z2 | 338.350991 | NMR | Benzo[d]isoxazol-3-yl-[1-(4-trifluoromethyl-sulfanylphenyl)-ethyl]-amine |

General Instructions for the Reductive Amination of the Amino-Substituted Benzisoxazole Skeleton Structure:

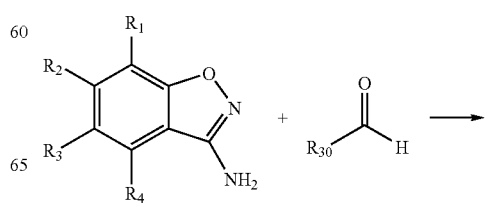

-continued

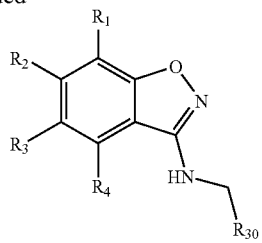

wherein $R^{30}$ denotes:

a linear or branched, saturated or unsaturated, unsubstituted or mono- or polysubstituted aliphatic group;

an unsubstituted or mono- or polysubstituted aryl or heteroaryl group, which can be condensed with a monocyclic or polycyclic ring system; or an unsubstituted or mono- or polysubstituted aryl or heteroaryl group, which can be condensed with a monocyclic or polycyclic ring system and is bonded via a linear or branched alkylene group.

Procedure:

Automated Synthesis

100 µmole of benzisoxazole solution (solution I, 0.05 M in DCM, 2 ml) were placed in a dry screw-neck vessel and 100 µmole of the corresponding aldehyde (solution II, 0.15 M in DCM, 0.66 ml) were added. A solution of a mixture of 120 µmole of triethylsilane and 300 µmole of trifluoroacetic acid (solution III, 0.1 M triethylsilane in DCM 0.25 M trifluoroacetic acid in DCM, 1.2 ml) was pipetted into the reaction solution. The screw-neck vessel was closed by a septum cap, and the reaction solution was stirred for 16 hours under reflux at 60° C. The reaction solution was then cooled to RT and made alkaline with 1.5 ml of 7% $NaCO_3$ solution, and thoroughly mixed for 30 minutes. The stirring fish was filtered off and the vessel was rinsed out with 1.5 ml of DCM.

The organic phase was separated and collected. 2 ml of DCM was added to the aqueous phase, vortexed, and thoroughly mixed for 15 minutes. After centrifugation the organic phase was separated and combined with the first fraction. The aqueous phase was extracted a second time in a similar manner with DCM. The combined organic phases were then dried over a $MgSO_4$ cartridge and concentrated in a GeneVac apparatus. The resulting product was purified by HPLC.

The following aldehydes were reacted according to this procedure:

| No. | Aldehyde | No. | Aldehyde |
|---|---|---|---|
| Z25 | 4-CCF3-phenylacetaldehyde | Z26 | 4-SCF3-phenylacetaldehyde |
| Z3 | 4-methylpentanal | Z27 | 4-propylphenylacetaldehyde |
| Z4 | 2-methylphenylacetaldehyde | Z28 | 3-(3-trifluoromethylphenoxy)phenylacetaldehyde |

-continued

| No. | Aldehyde | No. | Aldehyde |
| --- | --- | --- | --- |
| Z5 | 4-phenylbutanal | Z29 | [4-(difluoromethoxy)phenyl]acetaldehyde |
| Z6 | pentanal | Z30 | (3,5-dimethylphenyl)acetaldehyde |
| Z7 | anthracen-9-ylacetaldehyde | Z31 | (3-bromo-4-methoxyphenyl)acetaldehyde |
| Z8 | (4-chlorophenyl)acetaldehyde | Z32 | [4-(benzyloxy)-3,5-dimethylphenyl]acetaldehyde |
| Z9 | (3-nitrophenyl)acetaldehyde | Z33 | [3-(benzyloxy)phenyl]acetaldehyde |

-continued

| No. | Aldehyde | No. | Aldehyde |
|---|---|---|---|
| Z10 | 4-methoxy-3-(2-oxopropyl)phenylacetaldehyde | Z34 | 3-bromo-4,5-dimethoxyphenylacetaldehyde |
| Z11 | 2,4,5-trimethoxyphenylacetaldehyde | Z35 | 3-fluoro-2-methylphenylacetaldehyde |
| Z12 | 4-ethylphenylacetaldehyde | Z36 | 2-chloro-3-(trifluoromethyl)phenylacetaldehyde |
| Z13 | 3,4-dichlorophenylacetaldehyde | Z37 | 3-chloro-2-fluoro-5-(trifluoromethyl)phenylacetaldehyde |
| Z14 | 2,3,5-trifluorophenylacetaldehyde | Z38 | 2-fluoro-4-(trifluoromethyl)phenylacetaldehyde |

-continued

| No. | Aldehyde | No. | Aldehyde |
|---|---|---|---|
| Z15 | 4-phenoxyphenylacetaldehyde | Z39 | 4-(allyloxy)phenylacetaldehyde |
| Z16 | 3-chloro-4-fluorophenylacetaldehyde | Z40 | 2-(benzyloxy)-4,5-dimethoxyphenylacetaldehyde |
| Z17 | 4-(trifluoromethyl)phenylacetaldehyde | Z41 | 2-biphenylacetaldehyde |
| Z18 | 3-methylhexanal | Z42 | 3-iodophenylacetaldehyde |
| Z19 | 2,3,4-trifluorophenylacetaldehyde | Z43 | 3,4-dimethoxy-5-iodophenylacetaldehyde |

-continued

| No. | Aldehyde | No. | Aldehyde |
|---|---|---|---|
| Z20 | 2-fluoro-5-(trifluoromethyl)phenylacetaldehyde | Z44 | 2-cyanophenylacetaldehyde |
| Z21 | 4-methoxy-3-methylphenylacetaldehyde | Z45 | 4-hydroxyphenylacetaldehyde |
| Z22 | 3-chloro-2-fluorophenylacetaldehyde | Z46 | 3,4-dimethylphenylacetaldehyde |
| Z23 | 3,4-difluorophenylacetaldehyde | Z47 | 3-(trifluoromethyl)phenylacetaldehyde |
| Z24 | 2,6-dichlorophenylacetaldehyde | | |

The compounds of the following examples were synthesised according to the foregoing procedure. The identification numbers of the educts employed are given in the Table.

Employed Educts

| Example | Benzisoxazole | Aldehyde | Molecular weight | Identified by: (Purity) | Name |
|---|---|---|---|---|---|
| 136 | A | Z3 | 204.272996 | MS | Benzo[d]isoxazol-3-yl-(3-methylbutyl)-amine |
| 137 | K | Z4 | 256.279994 | MS (>80%) | (5-fluorobenzo[d]isoxazol-3-yl)-(2-methylbenzyl)-amine |

| Example | Benzisoxazole | Aldehyde | Molecular weight | Identified by: (Purity) | Name |
|---|---|---|---|---|---|
| 138 | D | Z5 | 295.385994 | MS (>80%) | N4,N4-dimethyl-N3-(3-phenylpropyl)-benzo[d]isoxazol-3,4-diamine |
| 139 | D | Z6 | 233.314996 | MS | N3-butyl-N4,N4-dimethylbenzo[d]isoxazol-3,4-diamine |
| 140 | E | Z7 | 354.408992 | MS | Anthracen-9-ylmethyl-(4-methoxybenzo[d]isoxazol-3-yl)-amine |
| 141 | E | Z8 | 288.733994 | MS (>80%) | (4-chlorobenzyl)-(4-methoxybenzo[d]isoxazol-3-yl)-amine |
| 142 | O | Z9 | 287.249994 | MS (>80%) | (6-fluorobenzo[d]isoxazol-3-yl)-(3-nitrobenzyl)-amine |
| 143 | M | Z10 | 346.769992 | MS (>80%) | Acetic acid-4-[(6-chloro-benzo[d]isoxazol-3-ylamino)-methyl]-2-methoxyphenyl ester |
| 144 | N | Z10 | 391.22599 | MS (>80%) | Acetic acid-4-[(6-bromo-benzo[d]isoxazol-3-ylamino)methyl]-2-methoxyphenyl ester |
| 145 | A | Z13 | 293.152993 | MS (>80%) | Benzo[d]isoxazol-3-yl-(3,4-dichlorobenzyl)amine |
| 146 | A | Z11 | 314.340993 | MS | Benzo[d]isoxazol-3-yl-(2,4,5-trimethoxy-benzyl)amine |
| 147 | A | Z12 | 252.316995 | MS (>80%) | benzo[d]isoxazol-3-yl-(4-ethylbenzyl)amine |
| 148 | M | Z13 | 327.597993 | MS (>80%) | (6-chloro-benzo[d]isoxazol-3-yl)-(3,4-dichlorobenzyl)-amine |
| 149 | A | Z14 | 278.232993 | MS (>80%) | benzo[d]isoxazol-3-yl-(2,3,5-trifluorobenzyl)-amine |
| 150 | M | Z15 | 350.804992 | MS (>80%) | (6-chlorobenzo[d]isoxazol-3-yl)-(4-phenoxybenzyl)-amine |
| 151 | G | Z16 | 294.687993 | MS (>80%) | (3-chloro-4-fluorobenzyl)-(7-fluorobenzo[d]isoxazol-3-yl)-amine |
| 152 | A | Z17 | 292.259992 | MS (>80%) | benzo[d]isoxazol-3-yl-(4-trifluoromethylbenzyl)-amine |
| 153 | G | Z18 | 236.289995 | MS (>80%) | (7-fluorobenzo[d]isoxazol-3-yl)-(2-methylpentyl)-amine |
| 154 | D | Z19 | 321.301992 | MS (>80%) | N4,N4-dimethyl-N3-(2,3,4-trifluorobenzyl)-benzo[d]-isoxazole-3,4-diamine |
| 155 | D | Z20 | 353.318991 | MS (>80%) | N3-(2-fluoro-5-trifluoro-methylbenzyl)-N4,N4-dimethylbenzo[d]isoxazole-3,4-diamine |
| 156 | H | Z21 | 283.330994 | MS (>80%) | N3-(4-methoxy-3-methyl-benzyl)benzo[d]isoxazole-3,4-diamine |
| 157 | H | Z21 | 283.330994 | MS | N3-(4-methoxy-3-methyl-benzyl)-benzo[d]isoxazole-3,4-diamine |
| 158 | A | Z25 | 308.258992 | MS (>80%) | benzo[d]isoxazol-3-yl-(4-trifluoromethoxybenzyl)-amine |
| 159 | K | Z25 | 326.248991 | MS (>80%) | (5-fluorobenzo[d]isoxazol-3-yl)-(4-trifluoromethoxy-benzyl)-amine |
| 160 | A | Z26 | 324.323992 | MS (>80%) | benzo[d]isoxazol-3-yl-(4-trifluoromethylsulfanyl-benzyl)-amine |
| 161 | M | Z27 | 314.815993 | MS (>80%) | (4-butylbenzyl)-(6-chloro-benzo[d]isoxazol-3-yl)-amine |
| 162 | K | Z26 | 342.313991 | MS (>80%) | (5-fluorobenzo[d]isoxazol-3-yl)-(4-trifluoromethyl-sulfanylbenzyl)-amine |

-continued

| Example | Benzisoxazole | Aldehyde | Molecular weight | Identified by: (Purity) | Name |
|---|---|---|---|---|---|
| 163 | A | Z38 | 310.249992 | MS (>80%) | benzo[d]isoxazol-3-yl-(2-fluoro-4-trifluoromethyl-benzyl)-amine |
| 164 | G | Z25 | 326.248991 | MS (>80%) | (7-fluorobenzo[d]isoxazol-3-yl)-(4-trifluoromethoxy-benzyl)-amine |
| 165 | G | Z28 | 402.346989 | MS (>80%) | (7-fluorobenzo[d]isoxazol-3-yl)-(3-(3-trifluoromethyl-phenoxy)-benzyl]-amine |
| 166 | E | Z29 | 320.294992 | MS (>80%) | (4-difluoromethoxy-benzyl)-(4-methoxy-benzo[d]-isoxazol-3-yl)-amine |
| 167 | G | Z30 | 270.306994 | MS (>80%) | (3,5-dimethylbenzyl)-(7-fluorobenzo[d]isoxazol-3-yl)-amine |
| 168 | O | Z31 | 351.17999 | MS (>80%) | (3-bromo-4-methoxy-benzyl)-(6-fluorobenzo[d]-isoxazol-3-yl)-amine |
| 169 | O | Z30 | 270.306994 | MS (>80%) | (3,5-dimethylbenzyl)-(6-fluorobenzo[d]isoxazol-3-yl)-amine |
| 170 | O | Z32 | 376.430991 | MS | (4-benzyloxy-3,5-dimethyl-benzyl)-(6-fluorobenzo[d]isoxazol-3-yl)-amine |
| 171 | O | Z27 | 298.360993 | MS (>80%) | (4-butylbenzyl)-(6-fluorobenzo[d]isoxazol-3-yl)-amine |
| 172 | O | Z26 | 342.313991 | MS (>80%) | (6-fluorobenzo[d]isoxazol-3-yl)-(4-trifluoromethyl-sulfanyl-benzyl)-amine |
| 173 | O | Z33 | 348.376992 | MS (>80%) | (3-benzyloxybenzyl)-(6-fluorobenzo[d]isoxazol-3-yl)-amine |
| 174 | H | Z30 | 267.331995 | MS | N3-(3,5-dimethylbenzyl)-benzo[d]isoxazole-3,4-diamine |
| 175 | H | Z27 | 295.385994 | MS | N3-(4-butylbenzyl)-benzo[d]isoxazole-3,4-diamine |
| 176 | L | Z26 | 403.224988 | MS (>80%) | (5-bromobenzo[d]isoxazol-3-yl)-(4-trifluoromethyl-sulfanyl-benzyl)-amine |
| 177 | G | Z34 | 381.20599 | MS (>80%) | (3-bromo-4,5-dimethoxy-benzyl)-(7-fluoro-benzo[d]isoxazol-3-yl)-amine |
| 178 | G | Z38 | 328.239991 | MS (>80%) | (7-fluorobenzo[d]isoxazol-3-yl)-(2-fluoro-4-trifluoro-methylbenzyl)-amine |
| 179 | D | Z35 | 299.348994 | MS (>80%) | N3-(3-fluoro-2-methyl-benzyl)-N4,N4-dimethylbenzo[d]isoxazole-3,4-diamine |
| 180 | D | Z36 | 369.773991 | MS (>80%) | N3-(2-chloro-3-trifluoro-methylbenzyl)-N4,N4-dimethyl-benzo[d]isoxazole-3,4-diamine |
| 181 | D | Z37 | 387.76399 | MS | N3-(3-chloro-2-fluoro-5-trifluoromethylbenzyl)-N4,N4-dimethyl-benzo[d]-isoxazole-3,4-diamine |
| 182 | O | Z38 | 328.239991 | MS (>80%) | (6-fluorobenzo[d]isoxazol-3-yl)-(2-fluoro-4-trifluoro-methylbenzyl)-amine |
| 183 | O | Z39 | 298.316993 | MS (>80%) | (4-allyloxybenzyl)-(6-fluorobenzo[d]isoxazol-3-yl)-amine |
| 184 | A | Z40 | 390.438991 | MS (>80%) | Benzo[d]isoxazol-3-yl-(2-benzyloxy-4,5-dimethoxy-benzyl)-amine |
| 185 | M | Z40 | 424.88399 | MS | (2-benzyloxy-4,5-dimethoxybenzyl)-(6-chlorobenzo[d]isoxazol-3-yl)-amine |

-continued

| Example | Benzisoxazole | Aldehyde | Molecular weight | Identified by: (Purity) | Name |
|---|---|---|---|---|---|
| 186 | D | Z40 | 433.507991 | MS (>80%) | N3-(2-benzyloxy-4,5-dimethoxybenzyl)-N4,N4-dimethylbenzo[d]isoxazole-3,4-diamine |
| 187 | D | Z41 | 343.429993 | MS | N3-biphenyl-2-ylmethyl-N4,N4-dimethyl-benzo[d]-isoxazole-3,4-diamine |
| 188 | O | Z42 | 368.148994 | MS (>80%) | (6-fluorobenzo[d]isoxazol-3-yl)-(3-iodobenzyl)-amine |
| 189 | E | Z40 | 420.464991 | MS (>80%) | (2-benzyloxy-4,5-dimethoxybenzyl)-(4-methoxy-benzo[d]isoxazol-3-yl)-amine |
| 190 | B | Z43 | 428.200992 | MS (>80%) | (4-fluorobenzo[d]isoxazol-3-yl)-(3-iodo-4,5-dimethoxybenzyl)-amine |
| 191 | J | Z44 | 263.299995 | MS | 2-[(5-methyl-benzo[d]-isoxazol-3-ylamino)-methyl]-benzonitrile |
| 192 | F | Z6 | 288.268993 | MS (>80%) | butyl-[4-(2,2,2-trifluoro-ethoxybenzo[d]isoxazol-3-yl]-amine |
| 193 | J | Z34 | 377.24299 | MS (>80%) | (3-bromo-4,5-dimethoxy-benzyl)-(5-methylbenzo[d]-isoxazol-3-yl)-amine |
| 198 | C | Z45 | 274.706994 | MS (>80%) | 4-[(4-chloro-benzo[d]isoxazol-3-ylamino)-methyl]-phenol |
| 199 | M | Z46 | 286.761994 | MS (>80%) | (6-chlorobenzo[d]isoxazol-3-yl)-(3,4-dimethylbenzyl)-amine |
| 200 | C | Z22 | 311.142993 | MS (>80%) | (4-chlorobenzo[d]isoxazol-3-yl)-(3-chloro-2-fluoro-benzyl)-amine |
| 201 | K | Z23 | 278.232993 | MS (>80%) | (3,4-difluorobenzyl)-(5-fluorobenzo[d]isoxazol-3-yl)-amine |
| 202 | N | Z24 | 372.05399 | MS (>80%) | (6-bromobenzo[d]isoxazol-3-yl)-(2,6-dichlorobenzyl)-amine |
| 203 | G | Z47 | 326.248991 | MS (>80%) | (7-fluorobenzo[d]isoxazol-3-yl)-(3-trifluoromethoxy-benzyl)-amine |

Synthesis of the Thioureas

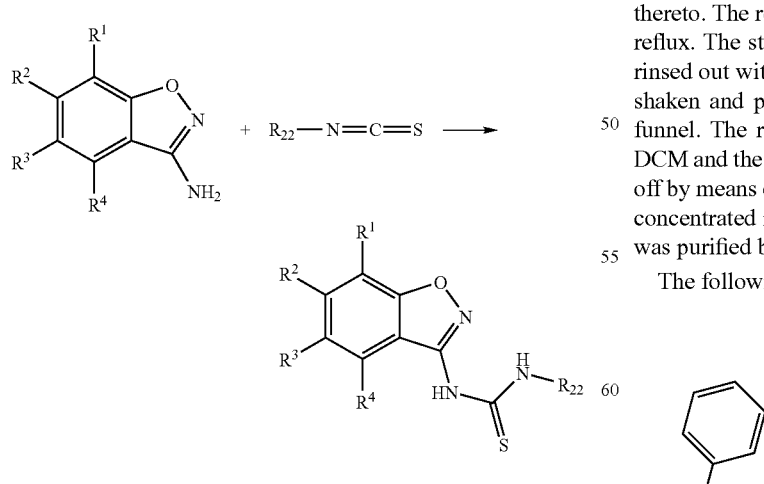

Automated Synthesis

100 μmole of benzisoxazole derivative solution (solution I; 0.1 M in pyridine, 1 ml) were placed in a dry screw-neck vessel at RT, and 100 μmole of isothiocyanate derivative solution (solution II; 0.1 M in pyridine, 1 ml) were added thereto. The reaction solution was stirred for 24 hours under reflux. The stirring fish was filtered out and the vessel was rinsed out with 2 ml of $CH_2Cl_2$. The suspension was briefly shaken and poured directly through a 0.45 μm GHP filter funnel. The reaction vessel was rinsed out with 7.5 ml of DCM and the suspension in the filter funnel was then filtered off by means of compressed air. The clear organic phase was concentrated in a Gene-Vac apparatus. The reaction product was purified by HPLC.

The following isothiocyanates were used:

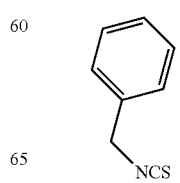

I1

-continued
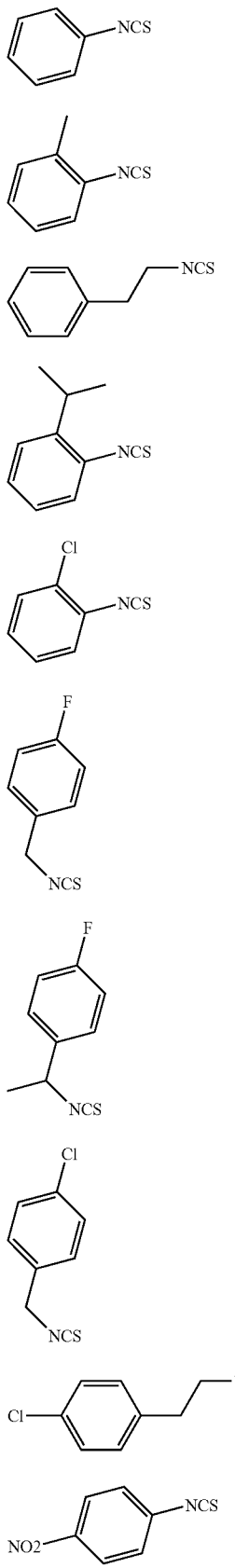
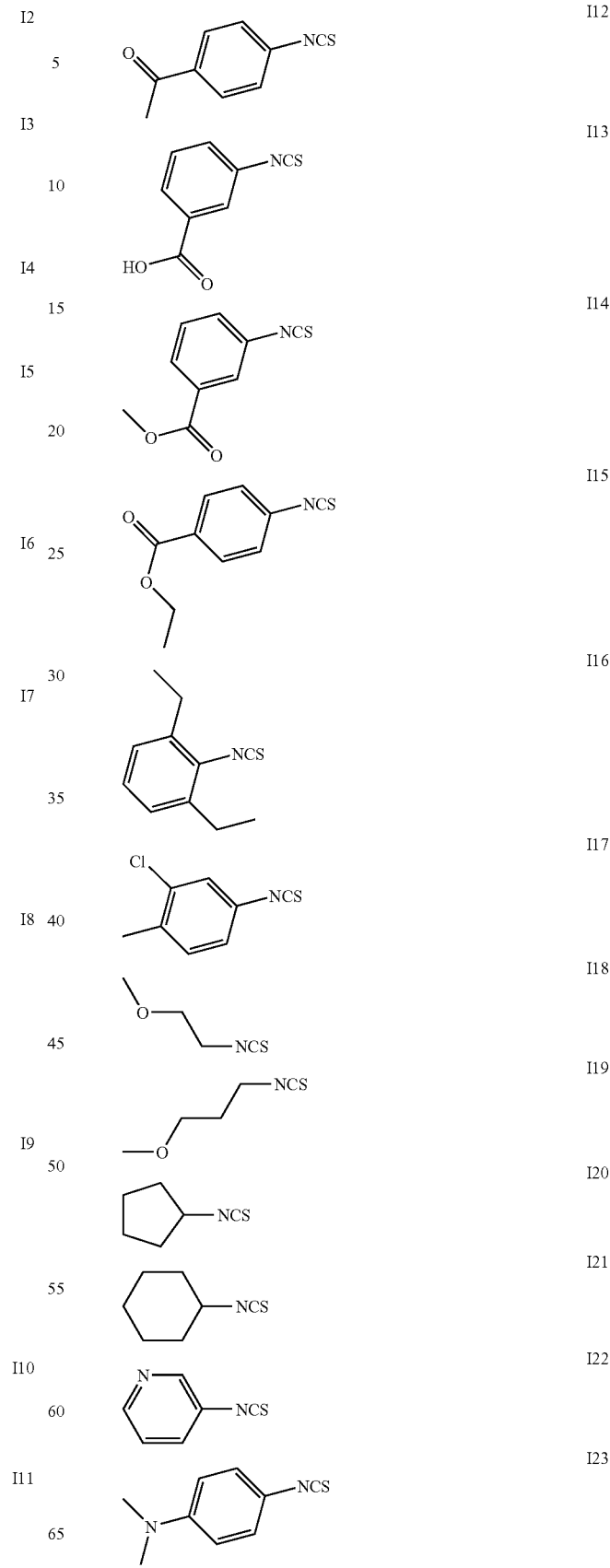

-continued
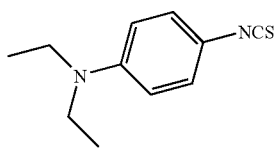
I24
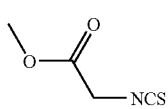
I25
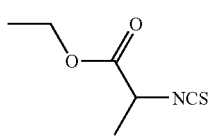
I26
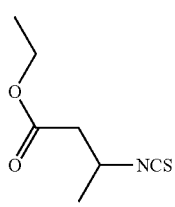
I27
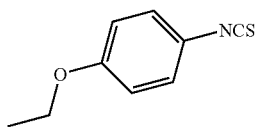
I28
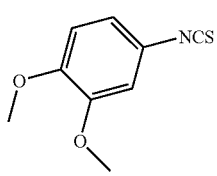
I29
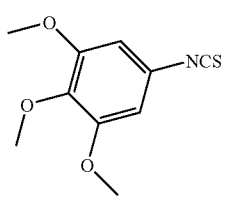
I30
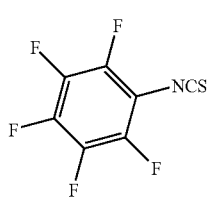
I31
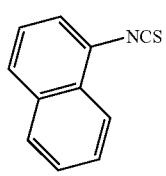
I32
-continued
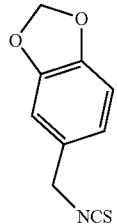
I33
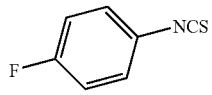
I34
I35
I36
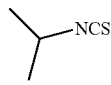
I37
I38
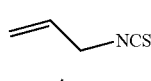
I39
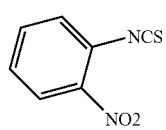
I40
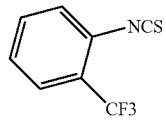
I41
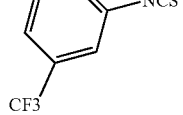
I42
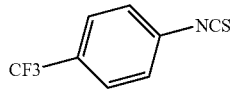
I43
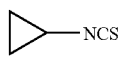
I44
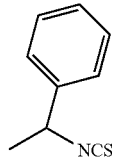
I45
I46
I47

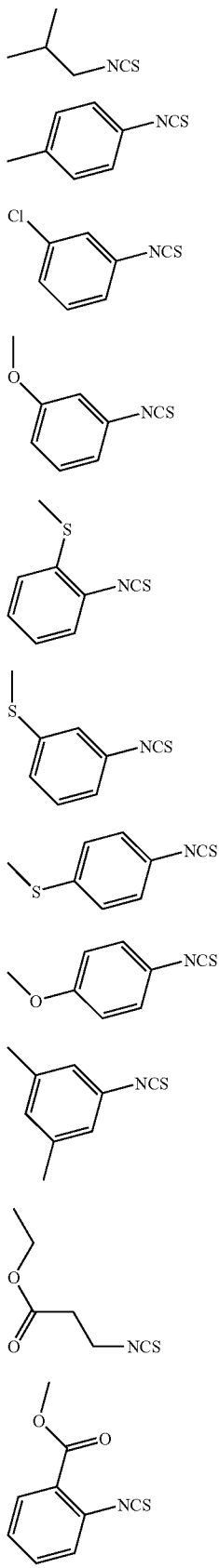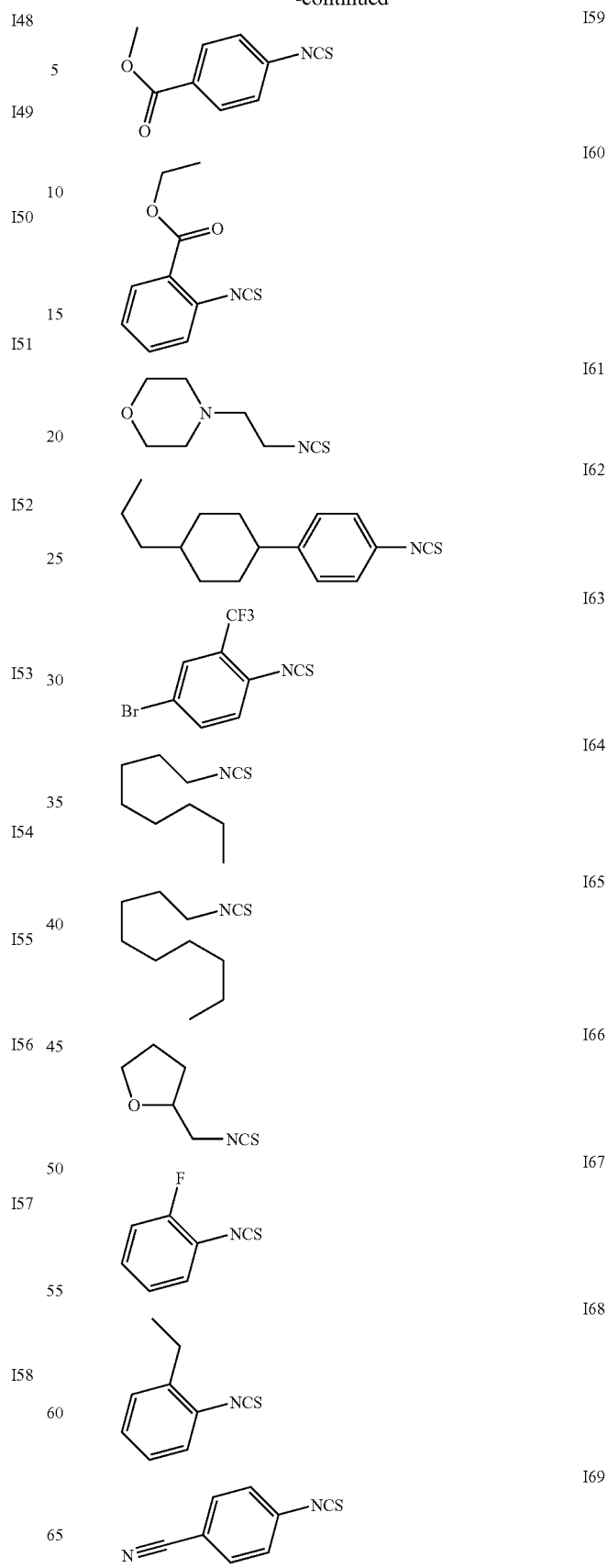

-continued

I70 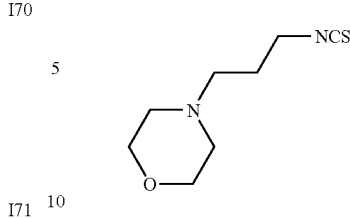

I71 

I72 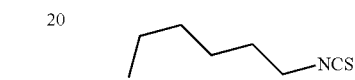

I73 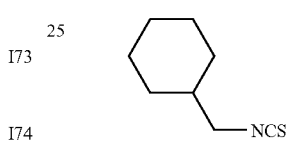

I74 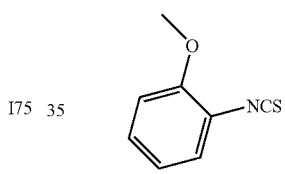

I75 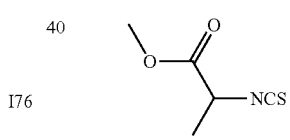

I76

-continued

I77

I78

I79

I80

I81

I82

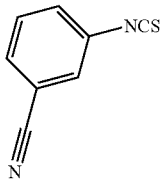

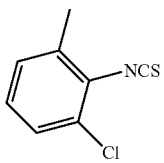

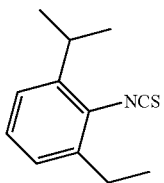

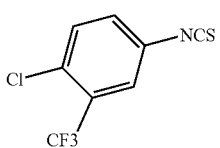

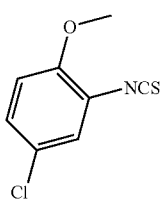

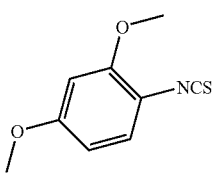

The following example compounds were synthesised as described above:

Employed Educts

| Example | Benzisoxazole | Isothiocyanate | Exact mass | Identified by: (Purity) | Name |
|---|---|---|---|---|---|
| 3 | A | I1 | 283.352994 | MS (>80%) | 1-benzo[d]isoxazol-3-yl-3-benzyl-thiourea |
| 4 | A | I2 | 269.325994 | MS (>80%) | 1-benzo[d]isoxazol-3-yl-3-phenyl-thiourea |
| 5 | A | I3 | 283.352994 | MS (>80%) | 1-benzo[d]isoxazol-3-yl-3-o-tolyl-thiourea |
| 6 | A | I4 | 297.379994 | MS (>80%) | 1-benzo[d]isoxazol-3-yl-3-phenethyl-thiourea |
| 7 | A | I5 | 311.406994 | MS (>80%) | 1-benzo[d]isoxazol-3-yl-3-(2-isopropylphenyl)-thiourea |
| 8 | A | I6 | 303.770993 | MS (>80%) | 1-benzo[d]isoxazol-3-yl-3-(2-chlorophenyl)-thiourea |

-continued

| Example | Benzisoxazole | Isothiocyanate | Exact mass | Identified by: (Purity) | Name |
|---|---|---|---|---|---|
| 9 | A | I7 | 301.342993 | MS (>80%) | 1-benzo[d]isoxazol-3-yl-3-(4-fluorobenzyl)-thiourea |
| 10 | A | I8 | 315.369993 | MS (>80%) | 1-benzo[d]isoxazol-3-yl-3-[1-(4-fluorophenyl)-ethyl]-thiourea |
| 11 | A | | 317.797993 | MS (>80%) | 1-benzo[d]isoxazol-3-yl-3-(4-chlorobenzyl)-thiourea |
| 12 | A | I10 | 331.824993 | MS (>80%) | 1-benzo[d]isoxazol-3-yl-3-[2-(4-chlorophenyl)-ethyl]-thiourea |
| 13 | A | I11 | 314.322994 | MS (>80%) | 1-benzo[d]isoxazol-3-yl-3-(4-nitrophenyl)-thiourea |
| 14 | A | I12 | 311.362993 | MS (>80%) | 1-(4-acetyl-phenyl)-3-benzo[d]isoxazol-3-yl-thiourea |
| 15 | A | I13 | 313.334993 | MS (>80%) | 3-(3-benzo[d]isoxazol-3-yl-thioureido)-benzoic acid |
| 16 | A | I14 | 327.361993 | MS (>80%) | 3-(3-benzo[d]isoxazol-3-yl-thioureido)-benzoic acid methyl ester |
| 17 | A | I15 | 341.368993 | MS (>80%) | 4-(3-benzo[d]isoxazol-3-yl-thioureido)-benzoic acid ethyl ester |
| 18 | A | I16 | 325.433993 | MS (>80%) | 1-benzo[d]isoxazol-3-yl-3-(2,6-diethylphenyl)-thiourea |
| 19 | A | I17 | 317.797993 | MS (>80%) | 1-benzo[d]isoxazol-3-yl-3-(3-chloro-4-methylphenyl)-thiourea |
| 20 | A | I18 | 251.307995 | MS (>80%) | 1-benzo[d]isoxazol-3-yl-3-(2-methoxyethyl)-thiourea |
| 21 | A | I19 | 265.334995 | MS (>80%) | 1-benzo[d]isoxazol-3-yl-3-(3-methoxypropyl)-thiourea |
| 22 | A | I20 | 261.346995 | MS (>80%) | 1-benzo[d]isoxazol-3-yl-3-cyclopentyl-thiourea |
| 23 | A | I21 | 275.373994 | MS (>80%) | 1-benzo[d]isoxazol-3-yl-3-cyclohexyl-thiourea |
| 24 | A | I22 | 270.313995 | MS (>80%) | 1-benzo[d]isoxazol-3-yl-3-pyridin-3-yl-thiourea |
| 25 | A | I23 | 312.394994 | MS (>80%) | 1-benzo[d]isoxazol-3-yl-3-(4-dimethylaminophenyl)-thiourea |
| 26 | A | I24 | 340.448993 | MS (>80%) | 1-benzo[d]isoxazol-3-yl-3-(4-diethylaminophenyl)-thiourea |
| 27 | A | I25 | 265.290995 | MS(>80%) | (3-benzo[d]isoxazol-3-yl-thioureido)-acetic acid methyl ester |
| 28 | A | I26 | 293.344994 | MS(>80%) | 2-(3-benzo[d]isoxazol-3-yl-thioureido)-propionic acid ethyl ester |
| 29 | A | I27 | 307.371994 | MS(>80%) | 3-(3-benzo[d]isoxazol-3-yl-thioureido)-butyric acid ethyl ester |
| 30 | A | I80 | 289.400994 | MS (>80%) | 1-benzo[d]isoxazol-3-yl-3-cyclohexylmethyl-thiourea |
| 31 | A | I28 | 313.378993 | MS(>80%) | 1-benzo[d]isoxazol-3-yl-3-(4-ethoxyphenyl)-thiourea |
| 32 | A | I29 | 329.377993 | MS(>80%) | 1-benzo[d]isoxazol-3-yl-3-(3,4-dimethoxyphenyl)-thiourea |
| 33 | A | I30 | 359.403992 | MS (>80%) | 1-benzo[d]isoxazol-3-yl-3-(3,4,5-trimethoxyphenyl)-thiourea |
| 34 | A | I31 | 359.27599 | MS (>80%) | 1-benzo(d)isoxazol-3-yl-3-pentafluorophenyl-thiourea |
| 35 | A | I32 | 319.385993 | MS (>80%) | 1-benzo[d]isoxazol-3-yl-3-naphthalen-1-yl-thiourea |
| 36 | A | I33 | 327.361993 | MS (>80%) | 1-benzo[1,3]dioxol-5-ylmethyl-3-benzo[d]isoxazol-3-yl-thiourea |
| 37 | A | I34 | 287.315994 | MS (>80%) | 1-benzo[d]isoxazol-3-yl-3-(4-fluorophenyl)-thiourea |
| 38 | A | I35 | 207.254996 | MS (>80%) | 1-benzo[d]isoxazol-3-yl-3-methyl-thiourea |
| 39 | A | I36 | 221.281996 | MS (>80%) | 1-benzo[d]isoxazol-3-yl-3-thiourea |
| 40 | A | I37 | 235.308995 | MS (>80%) | 1-benzo[d]isoxazol-3-yl-3-propyl-thiourea |
| 41 | A | I38 | 235.308995 | MS (>80%) | 1-benzo[d]isoxazol-3-yl-3-isopropyl-thiourea |
| 42 | A | I39 | 249.335995 | MS (>80%) | 1-benzo[d] isoxazol-3-yl-3-tert-butyl-thiourea |
| 43 | A | I40 | 233.292995 | MS | 1-allyl-3-benzo[d]isoxazol-3-thiourea |

-continued

| Example | Benzisoxazole | Isothio-cyanate | Exact mass | Identified by: (Purity) | Name |
|---------|---------------|-----------------|------------|------------------------|------|
| 44 | A | I41 | 247.319995 | MS (>80%) | 1-benzo[d]isoxazol-3-yl-3-(2-methyl-allyl)-thiourea |
| 45 | A | I42 | 314.322994 | NMR | 1-benzo[d]isoxazol-3-yl-3-(2-nitro-phenyl)-thiourea |
| 46 | A | I43 | 337.322992 | MS (>80%) | 1-benzo[d]isoxazol-3-yl-3-(2-trifluoromethylphenyl-thiourea |
| 47 | A | I44 | 337.322992 | MS (>80%) | 1-benzo[d]isoxazol-3-yl-3-(3-trifluoromethylphenyl)-thiourea |
| 48 | A | I45 | 337.322992 | MS (>80%) | 1-benzo[d]isoxazol-3-yl-3-(4-trifluoromethylphenyl)-thiourea |
| 49 | A | I46 | 233.292995 | MS (>80%) | 1-benzo[d]isoxazol-3-yl-3-cyclopropyl-thiourea |
| 50 | B | I82 | 297.307993 | MS (>80%) | 2-[3-(4-fluoro-benzo[d]isoxazol-3-yl)-thioureido]-propionic acid methyl ester |
| 51 | C | I3 | 317.797993 | MS | 1-(4-chlorobenzo[d]isoxazol-3-yl)-3-o-tolyl-thiourea |
| 52 | C | I1 | 317.797993 | MS (>80%) | 1-benzyl-3-(4-chloro-benzo[d]isoxazol-3-yl)-thiourea |
| 53 | C | I47 | 331.824993 | MS (>80%) | 1-(4-chlorobenzo[d]isoxazol-3-yl)-3-(1-phenyl-ethyl)-thiourea |
| 54 | D | I48 | 292.404994 | MS | 1-(4-dimethylamino-benzo[d]isoxazol-3-yl)-3-isobutyl-thiourea |
| 55 | D | I49 | 326.421993 | MS | 1-(4-dimethylamino-benzo[d]-isoxazol-yl)-3-p-tolyl-thiourea |
| 56 | D | I50 | 346.839993 | MS (>80%) | 1-(3-chlorophenyl)-3-(4-dimethylaminobenzo[d]isoxazol-3-yl)-thiourea |
| 57 | D | I51 | 342.420993 | MS (>80%) | 1-(4-dimethylamino-benzo[d]isoxazol-3-yl)-3-(3-methoxyphenyl)-thiourea |
| 58 | D | I52 | 358.485993 | MS (>80%) | 1-(4-dimethylamino-benzo[d]isoxazol-3-yl)-3-(2-methylsulfanylphenyl)-thiourea |
| 59 | D | I53 | 358.485993 | MS (>80%) | 1-(4-dimethylaminobenzo[d]isoxazol-3-yl)-3-(3-methylsulfanylphenyl)-thiourea |
| 60 | D | I54 | 358.485993 | MS (>80%) | 1-(4-dimethylamino-benzo[d]isoxazol-3-yl)-3-(4-methylsulfanylphenyl)-thiourea |
| 61 | D | I81 | 342.420993 | MS (>80%) | 1-(4-dimethylamino-benzo[d]isoxazol-3-yl)-3-(2-methoxyphenyl)-thiourea |
| 62 | D | I55 | 342.420993 | MS (>80%) | 1-(4-dimethylamino-benzo[d]isoxazol-3-yl)-3-(4-methoxyphenyl)-thiourea |
| 63 | D | I56 | 340.448993 | MS (>80%) | 1-(4-dimethylamino-benzo[d]isoxazol-3-yl)-3-(3,5-dimethylphenyl)-thiourea |
| 64 | D | I1 | 326.421993 | MS (>80%) | 1-benzyl-3-(4-dimethylamino-benzo[d]isoxazol-3-yl)-thiourea |
| 65 | D | I19 | 308.403994 | MS (>80%) | 1-(4-dimethylamino-benzo[d]isoxazol-3-yl)-3-(3-methoxypropyl)-thiourea |
| 66 | D | I57 | 336.413993 | MS (>80%) | 3-[3-(4-dimethylamino-benzo-[d]isoxazol-3-yl)-thioureido]-propionic acid ethyl ester |
| 67 | D | I26 | 336.413993 | MS (>80%) | 2-[3-(4-dimethylamino-benzo-[d]isoxazol-3-yl)-thioureido]-propionic acid ethyl ester |
| 68 | D | I27 | 350.440993 | MS (>80%) | 3-[3-(4-dimethylamino-benzo-[d]isoxazol-3-yl)-thioureido]-butyric acid ethyl ester |
| 69 | D | I13 | 356.403993 | MS (>80%) | 3-[3-(4-dimethylamino-benzo[d]isoxazol-3-yl)-thioureidol-benzoic acid |
| 70 | D | I28 | 356.447993 | MS (>80%) | 1-(4-dimethylaminobenzo[d]isoxazol-3-yl)-3-(4-ethoxyphenyl)-thiourea |
| 71 | D | I58 | 370.430992 | MS (>80%) | 2-[3-(4-dimethylamino-benzo[d]-isoxazol-3-yl)-thioureido]-benzoic acid methyl ester |

-continued

| Example | Benzisoxazole | Isothio-cyanate | Exact mass | Identified by: (Purity) | Name |
|---|---|---|---|---|---|
| 72 | D | I14 | 370.430992 | MS | 3-(3-(4-dimethylamino-benzo-[d]isoxazol-3-yl)-thioureido)-benzoic acid methyl ester |
| 73 | D | I59 | 370.430992 | MS (>80%) | 4-(3-(4-dimethylamino-benzo-[d]isoxazol-3-yl)-thioureido)-benzoic acid methyl ester |
| 74 | D | I60 | 384.457992 | MS (>80%) | 2-[3-(4-dimethylamino-benzo-[d]isoxazol-3-yl)-thioureido]-benzoic acid ethyl ester |
| 75 | D | I15 | 384.457992 | MS (>80%) | 4-(3-(4-dimethylamino-benzo-[d]isoxazol-3-yl)-thioureido]-benzoic acid ethyl ester |
| 76 | D | I12 | 354.431993 | MS | 1-(4-acetylphenyl)-3-(4-dimethylaminobenzo[d]isoxazol-3-yl)-thiourea |
| 77 | E | I6 | 333.796993 | MS (>80%) | 1-(2-chlorophenyl)-3-(4-methoxy-benzo[d]isoxazol-3-yl)-thiourea |
| 78 | E | I24 | 370.474993 | MS (>80%) | 1-(4-diethylaminophenyl)-3-(4-methoxybenzo[d]isoxazol-3-yl)-thiourea |
| 79 | E | I61 | 336.413993 | MS (>80%) | 1-(4-methoxybenzo[d]isoxazol-3-yl)-3-(2-morpholin-4-yl-ethyl)-thiourea |
| 80 | F | I82 | 377.340991 | MS (>80%) | 2-(3-[4-(2,2,2-trifluoroethoxy)-benzo[d]isoxazol-3-yl]-thioureido)-propionic acid methyl ester |
| 81 | F | I33 | 425.38499 | MS (>80%) | 1-benzo[1,3]dioxol-5-ylmethyl-3-[4-(2,2,2-trifluoroethoxy)-benzo[d]isoxazol-3-yl]-thiourea |
| 82 | F | I62 | 491.575988 | MS (>80%) | 1-[4-(4-propylcyclohexyl)-phenyl]-3-[4-(2,2,2-trifluoroethoxy)-benzo[d]isoxazol-3-yl]-thiourea |
| 83 | F | I63 | 514.246985 | MS (>80%) | 1-(4-bromo-2-trifluoromethyl-phenyl)-3-[4-(2,2,2-trifluoroethoxy)-benzo[d]isoxazol-3-yl]-thiourea |
| 84 | F | I55 | 397.37499 | MS (>80%) | 1-(4-methoxyphenyl)-3-[4-(2,2,2-trifluoroethoxy)-benzo[d]isoxazol-3-yl]-thiourea |
| 85 | F | I57 | 391.36799 | MS (>80%) | 3-(3-[4-(2,2,2-trifluoroethoxy)-benzo[d]isoxazol-3-yl]-thioureido)-propionic acid ethyl ester |
| 86 | I | I64 | 425.594991 | MS (>80%) | 1-(4-(4-methylbenzyloxy)-benzo[d]isoxazol-3-yl]-3-octyl-thiourea |
| 87 | I | I65 | 439.621991 | MS (>80%) | 1-[4-(4-methylbenzyloxy)-benzo[d]isoxazol-3-yl]-3-nonyl-thiourea |
| 88 | I | I46 | 353.443992 | MS (>80%) | 1-cyclopropyl-3-[4-(4-methylbenzyloxy)-benzo[d]isoxazol-3-yl]-thiourea |
| 89 | I | I20 | 381.497992 | MS (>80%) | 1-cyclopentyl-3-[4-(4-methylbenzyloxy)-benzo[d]isoxazol-3-yl]-thiourea |
| 90 | I | I21 | 395.524992 | MS (>80%) | 1-cyclohexyl-3-[4-(4-methylbenzyloxy)-benzo[d]isoxazol-3-yl]-thiourea |
| 91 | I | I80 | 409.551991 | MS (>80%) | 1-cyclohexylmethyl-3-[4-(4-methylbenzyloxy) benzo[d]isoxazol-3-yl]-thiourea |
| 92 | F | I23 | 410.41799 | MS (>80%) | 1-(4-dimethylaminophenyl)-3-[4-(2.2,2-trifluoroethoxy)-benzo[d]isoxazol-3-yl]-thiourea |
| 93 | J | I40 | 247.319995 | MS | 1-allyl-3-(5-methylbenzo[d]isoxazol-3-yl)-thiourea |
| 94 | J | I25 | 279.317994 | MS (>80%) | [3-(5-methylbenzo[d]isoxazol-3-yl)-thioureido]-acetic acid methyl ester |
| 95 | J | I5 | 325.433993 | MS (>80%) | 1-(2-isopropylphenyl)-3-(5-methyl-benzo[d]isoxazol-3-yl)-thiourea |

-continued

| Example | Benzisoxazole | Isothio-cyanate | Exact mass | Identified by: (Purity) | Name |
|---|---|---|---|---|---|
| 96 | J | I45 | 351.349991 | MS (>80%) | 1-(5-methylbenzo[d]isoxazol-3-yl)-3-(4-trifluoromethylphenyl)-thiourea |
| 97 | K | I82 | 297.307993 | MS (>80%) | 2-[3-(5-fluorobenzo(d]isoxazol-3-yl)-thioureido]-propionic acid methyl ester |
| 98 | K | I66 | 295.335994 | MS (>80%) | 1-(5-fluorobenzo[d]isoxazol-3-yl)-3-(tetrahydrofuran-2-yl-methyl)-thiourea |
| 99 | L | I67 | 366.21699 | MS (>80%) | 1-(5-bromobenzo[d]isoxazol-3-yl)-3-(2-fluorophenyl)-thiourea |
| 100 | L | I68 | 376.28099 | MS (>80%) | 1-(5-bromobenzo[d]isoxazol-3-yl)-3-(2-ethylphenyl)-thiourea |
| 101 | M | I34 | 321.760993 | MS (>80%) | 1-(6-chlorobenzo[d]isoxazol-3-yl)-3-(4-fluorophenyl)-thiourea |
| 102 | M | I67 | 321.760993 | MS (>80%) | 1-(6-chlorobenzo(d]isoxazol-3-yl)-3-(2-fluorophenyl)-thiourea |
| 103 | M | I20 | 295.791994 | MS (>80%) | 1-(6-chlorobenzo[d]isoxazol-3-yl)-3-cyclopentyl-thiourea |
| 104 | M | I69 | 328.780993 | MS (>80%) | 1-(6-chlorobenzo[d]isoxazol-3-yl)-3-(4-cyanophenyl)-thiourea |
| 105 | M | I13 | 347.779992 | MS (>80%) | 3-[3-(6-chlorobenzo[d]isoxazol-3-yl)-thioureido]-benzoic acid |
| 106 | M | I55 | 333.796993 | MS (>80%) | 1-(6-chlorobenzo[d]isoxazol-3-yl)-3-(4-methoxyphenyl)-thiourea |
| 107 | M | I51 | 333.796993 | MS (>80%) | 1-(6-chlorobenzo[d]isoxazol-3-yl-3-(3-methoxyphenyl)-thiourea |
| 108 | N | I29 | 408.27899 | MS (>80%) | 1-(6-bromobenzo[d]isoxazol-3-yl)-3-(3,4-dimethoxyphenyl)-thiourea |
| 109 | N | I32 | 398.28699 | MS | 1-(6-bromobenzo[d]isoxazol-3-yl)-3-naphthalen-1-yl-thiourea |
| 110 | N | I33 | 406.26299 | MS | 1-benzo[1,3]dioxol-5-ylmethyl-3-(6-bromobenzo[d]isoxazol-3-yl)-thiourea |
| 111 | O | I52 | 333.406992 | MS (>80%) | 1-(6-fluorobenzo[d]isoxazol-3-yl)-3-(2-methylsulfanylphenyl)-thiourea |
| 112 | O | I70 | 312.325993 | MS (>80%) | 1-(3-cyanophenyl)-3-(6-fluoro-benzo[d]isoxazol-3-yl)-thiourea |
| 113 | O | I71 | 335.787992 | MS (>80%) | 1-(2-chloro-6-methylphenyl)-3-(6-fluorobenzo[d]isoxazol-3-yl)-thiourea |
| 114 | O | I72 | 371.477992 | MS (>80%) | 1-(2,6-diisopropylphenyl)-3-(6-fluorobenzo[d]isoxazol-3-yl)-thiourea |
| 115 | G | I35 | 225.244995 | MS (>80%) | 1-(7-fluorobenzo[d]isoxazol-3-yl)-3-methyl-thiourea |
| 116 | G | I36 | 239.271995 | MS (>80%) | 1-ethyl-3-(7-fluorobenzo[d]-isoxazol-3-yl)-thiourea |
| 117 | G | I37 | 253.298995 | MS (>80%) | 1-(7-fluorobenzo[d]isoxazol-3-yl)-3-propyl-thiourea |
| 118 | G | I73 | 281.352994 | MS (>80%) | 1-(7-fluorobenzo[d]isoxazol-3-yl)-3-pentyl-thiourea |
| 119 | G | I79 | 295.379994 | MS (>80%) | 1-(7-fluorobenzo[d]isoxazol-3-yl)-3-hexyl-thiourea |
| 120 | G | I64 | 323.433993 | MS (>80%) | 1-(7-fluorobenzo[d]isoxazol-3-yl)-3-octyl-thiourea |
| 121 | G | I65 | 337.460993 | MS | 1-(7-fluorobenzo[d]isoxazol-3-yl)-3-nonyl-thiourea |
| 122 | G | I48 | 267.325994 | MS (>80%) | 1-(7-fluorobenzo[d]isoxazol-3-yl)-3-isobutyl-thiourea |
| 123 | G | I40 | 251.282995 | MS | 1-allyl-3-(7-fluorobenzo[d]-isoxazol-3-yl)-thiourea |
| 124 | G | I49 | 301.342993 | MS | 1-(7-fluorobenzo[d]isoxazol-3-yl)-3-p-tolyl-thiourea |
| 125 | L | I23 | 391.29599 | MS (>80%) | 1-(5-bromobenzo(d)isoxazol-3-yl)-3-(4-dimethylaminophenyl)-thiourea |
| 126 | G | I61 | 324.377993 | MS (>80%) | 1-(7-fluorobenzo[d]isoxazol-3-yl)-3-(2-morpholin-4-yl-ethyl)-thiourea |
| 127 | G | I77 | 338.404993 | MS (>80%) | 1-(7-fluorobenzo[d]isoxazol-3-yl)-3-(3-morpholin-4-yl-propyl)-thiourea |

-continued

| Example | Benzisoxazole | Isothiocyanate | Exact mass | Identified by: (Purity) | Name |
|---|---|---|---|---|---|
| 128 | E | I78 | 327.405993 | MS (>80%) | 1-(4-methoxybenzo[d]isoxazol-3-yl)-3-(1-phenylethyl)-thiourea |
| 129 | E | I9 | 347.823992 | MS (>80%) | 1-(4-chlorobenzyl)-3-(4-methoxybenzo[d]isoxazol-3-yl)-thiourea |
| 130 | F | I81 | 329.377993 | MS (>80%) | 1-(4-methoxybenzo[d]isoxazol-3-yl)-3-(2-methoxyphenyl)-thiourea |
| 131 | L | I23 | 391.29599 | MS | 1-(5-bromobenzo[d]isoxazol-3-yl)-3-(4-dimethylaminophenyl)-thiourea |
| 132 | E | I75 | 363.822992 | MS (>80%) | 1-(5-chloro-2-methoxyphenyl)-3-(4-methoxybenzo[d]isoxazol-3-yl)-thiourea |
| 133 | D | I74 | 401.79399 | MS (>80%) | 1-(4-chloro-3-trifluoromethyl-phenyl)-3-(4-methoxybenzo-[d]isoxazol-3-yl)-thiourea |
| 134 | E | I76 | 359.403992 | MS (>80%) | 1-(2,4-dimethoxyphenyl)-3-(4-methoxybenzo[d]isoxazol-3-yl)-thiourea |
| 135 | F | I30 | 457.426989 | MS (>80%) | 1-[4-(2,2,2-trifluoroethoxy)-benzo[d]isoxazol-3-yl]-3-(3,4,5-trimethoxyphenyl)-thiourea |

Pharmacological Test Methods

I. Fluorescence Assay (FLIPR™ Instrument) for the Identification of Substances Acting Agonistically on the KCNQ2/3 Ion Channel On the day before the experiment, KCNQ2/3-expressing CHO-K1 cells and CHO-K1 empty strain cells were seeded out onto coated poly-D-lysine black/clear plates (Falcon/BD Company; Order No.: 356640) in a concentration of 20000 cells/100 µl MEM alpha, 50 ml FCS, 5.5 ml PIS/G/solution (100×) and then incubated for 20-24 hours in an incubator (37° C., 5% $CO_2$). On the day of the experiment the HBSS/hepes working solution and the FMP/HBSS/hepes mixture (Membrane Potential Assay Kit Red (FMP), bulk format Cat. No. R8123) were initially prepared according to the following protocol:

1. HBSS/hepes:
   1000 ml 1× HBSS buffer (Hank's Balanced Salt Solution (1×) (Gibco; No. 14025)+10 ml hepes (1M stock solution, pH 7.4; hepes Na salt (Sigma Company; No. H7006-500 g; storage at 4° C. in a refrigerator)

2. 1× FMP/HBSS/hepes working solution:
   6 ml HBSS/hepes buffer are added to 5 ml of the FMP solution stored at −20° C. (preparation see below; thawing out at room temperature).

The test substances (2 mM batch solution in 100% DMSO) contained in drug plates (Costar 96-well plates, catalogue No. 3795) were then diluted by adding HBSS/hepes buffer to a concentration of 30 µM (3× concentrated). The assay plates on which the cells grow were washed once with 200 µl HBSS/hepes (Cellwash Washer, Labsystems Company, catalogue No. 5161550) and the remaining volume was removed by tapping out the inverted plate twice. 100 µl of the FMP/HBSS/hepes working solution were then added in each case to the cell plates and incubated for 1 hour in the $CO_2$ incubator at 37° C. and 5% $CO_2$. The measurements are then carried out with a FLIPR III instrument from the Molecular Devices company (96-format, using the 540-590 nm band-pass filter in the #2 localization). In the experimental setup of the FLIPR software, filter #2 should be selected. The cell plates and the substance plates were fed alternately into the input stack. A signal test was carried out in each case with the cell plates before adding the substance. The test substances were then added via the pipetting unit of the FLIPR (added volume 50 µl, 3× concentrated, end concentration 10 µM) to the cavities of the cell plates in a total volume of 150 µl/well. The threshold data of the FLIPR program were as follows:

| | |
|---|---|
| Pipetting volume: | 50 µl |
| Pipetting height: | 225 µl |
| Pipetting rate: | 50 µl/sec. |
| Camera configuration: | exposure = 0.4; gain = 50 |

The pipette tips were washed after each pipetting procedure 3 times with 1% DMSO in water. The times of the measurement intervals after addition of the test substances are as follows:

Sequence 1: 60×1 sec

Sequence 2: 15×20 sec

Total measurement time: 6 min/plate

The test samples were evaluated by calculating the difference between the maximum and minimum values. $EC_{50}/IC_{50}$ values are calculated using the Graph Pad Prism software.

Solutions:

Preparation of the membrane potential loading buffer (membrane potential assay kit red (FMP), bulk format cat. No. R8123) according to the manufacturer's instructions:

10 ml of the 10× assay buffer (component B) were diluted with 90 ml of sterile water and then adjusted to pH 7.4 with 1.0N NaOH (1× assay buffer). One vessel with the FLIPR membrane potential assay component A was completely dissolved in 100 ml 1× assay buffer and thoroughly mixed for 10 minutes with a magnetic stirrer. 5 ml aliquots were then stored at −20° C. (storage shelf life ca. 2 weeks).

An agonistic action can be detected starting from a value of −40 (and below).

| Example | FLIPR ΔF % Inhibition |
|---|---|
| 55 | −84 |
| 107 | −80 |
| 65 | −79 |
| 200 | −74 |
| 172 | −68 |
| 52 | −67.5 |
| 87 | −66.5 |
| 54 | −64 |
| 95 | −64 |
| 169 | −63.25 |
| 167 | −61 |
| 50 | −59.5 |
| 106 | −59 |
| 97 | −58.5 |
| 103 | −58 |
| 160 | −58 |
| 175 | −57.7 |
| 96 | −57 |
| 63 | −56 |
| 163 | −56 |
| 113 | −55 |
| 123 | −55 |
| 173 | −55 |
| 56 | −55 |
| 114 | −54 |
| 108 | −53.5 |
| 158 | −53 |
| 171 | −53 |
| 64 | −52 |
| 92 | −51 |
| 51 | −50 |
| 124 | −50 |
| 152 | −49 |
| 31 | −49 |
| 203 | −49 |
| 135 | −47.5 |
| 94 | −47 |
| 128 | −47 |
| 93 | −45.5 |
| 174 | −45.5 |
| 132 | −45 |
| 98 | −43.5 |
| 53 | −42.5 |
| 100 | −42 |
| 134 | −42 |
| 129 | −42 |
| 90 | −41.5 |
| 159 | −41 |
| 23 | −40 |
| 84 | −40 |
| 161 | −40 |

II. Voltage Clamp Measurements

In order to confirm electrophysiologically a KCNQ2/3 agonistic action of the substances, patch-clamp measurements [see Hamill O P, Marty A, Neher E, Sakmann B, Sigworth F J: "Improved patch-clamp techniques for high-resolution current recording from cells and cell-free membrane patches", *Pflugers Arch.* 1981 August; 391(2):85-100] were carried out in the voltage clamp mode on a stably transfected hKCNQ2/3 CHO-K1 cell line. After formation of the gigaseal the cells were first of all clamped at a holding potential of −60 mV. Depolarising voltage jumps were then applied up to a potential of +20 mV (increment: 20 mV, duration: 1 second), in order to confirm the functional expression of KCNQ2/3 typical currents. The substances were tested at a potential of −40 mV. The current increase induced by retigabin (10 μM) was first of all recorded on each cell at −40 mV as positive control. After completely washing out the retigabin effect (duration: 80 sec) the test substance (10 μM) was applied. The current increase induced by the test substance was standardized to the retigabin effect and stated as relative efficacy (see below).

| Example | Voltage clamp: relative efficacy with respect to retigabin [10 μM] |
|---|---|
| 163 | 1.29 |
| 173 | 0.84 |
| 174 | 0.8 |
| 162 | 0.79 |
| 170 | 0.72 |
| 171 | 0.68 |
| 176 | 0.62 |
| 161 | 0.61 |
| 175 | 0.59 |
| 160 | 0.45 |
| 159 | 0.42 |
| 1 | 0.42 |
| 2 | 0.37 |
| 168 | 0.35 |
| 112 | 0.3 |
| 167 | 0.25 |
| 152 | 0.22 |
| 130 | 0.2 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A substituted benzo[d]isoxazol-3-yl amine compound corresponding to formula I

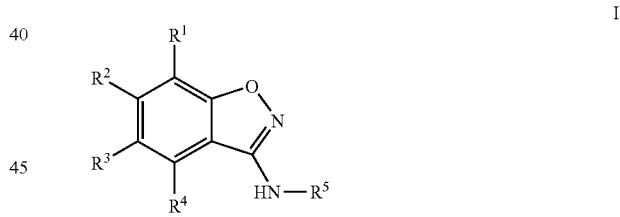

wherein $R^1$, $R^2$, $R^3$ and $R^4$ each independently denote H, F, Cl, Br, I, —CN, —$NO_2$, —$SF_5$, —$NR^7R^8$, —$OR^9$, —$SR^{10}$, —C(=O)$OR^{11}$, —(C=O)$NR^{12}R^{13}$, —S(=O)$_2R^{14}$, —C(=O)$R^{15}$, $NR^{16}$—S(=O)$_2R^{17}$, $C_{1-10}$-alkyl, $C_{2-10}$-alkenyl, or $C_{2-10}$-alkinyl;

$R^5$ denotes $(CHR^6)_n$—$R^{25}$, wherein n=1, 2 or 3;

$R^6$ denotes H, $C_{3-8}$-cycloalkyl or $C_{1-6}$-alkyl, and $R^{25}$ denotes aryl or heteroaryl;

$R^7$ and $R^8$ each independently denote H, —C(=O)$R^{14}$ or $C_{1-10}$-alkyl, or $R^7$ and $R^8$ together with the nitrogen atom to which they are bound form a morpholine, piperidine or pyrrolidine ring;

$R^9$, $R^{10}$, $R^{11}$ and $R^{16}$ each independently denote H, $C_{1-10}$-alkyl, $C_{2-10}$-alkenyl, $C_{2-10}$-alkinyl, $C_{3-8}$-cycloalkyl, —($C_{1-5}$-alkylene)-$C_{3-8}$-cycloalkyl, heterocycloalkyl, —($C_{1-5}$-alkylene)-heterocycloalkyl, aryl, heteroaryl, —($C_{1-5}$-alkylene)-aryl, or —($C_{1-5}$-alkylene)-heteroaryl;

$R^{12}$ and $R^{13}$ each independently denote H or $C_{1-10}$-alkyl, or $R^{12}$ and $R^{13}$ together with the nitrogen atom to which they are bound form a morpholine, piperidine or pyrrolidine ring;

$R^{14}$ denotes —$NR^7R^8$, $C_{1-10}$-alkyl, $C_{2-10}$-alkenyl, $C_{2-10}$-alkinyl, $C_{3-8}$-cycloalkyl, —($C_{1-5}$-alkylene)-$C_{3-8}$-cycloalkyl, heterocycloalkyl, —($C_{1-5}$-alkylene)-heterocycloalkyl, aryl, heteroaryl, —($C_{1-5}$-alkylene)-aryl or —($C_{1-5}$-alkylene)-heteroaryl; and $R^{15}$ and $R^{17}$ each independently denote $C_{1-10}$-alkyl, $C_{2-10}$-alkenyl, $C_{2-10}$-alkinyl, $C_{3-8}$-cycloalkyl, —($C_{1-5}$-alkylene)-$C_{3-8}$-cycloalkyl, heterocycloalkyl, —($C_{1-5}$-alkylene)-heterocycloalkyl, aryl, heteroaryl, —($C_{1-5}$-alkylene)-aryl or —($C_{1-5}$-alkylene)-heteroaryl;

wherein the aforementioned $C_{1-10}$-alkyl, $C_{2-10}$-alkenyl and $C_{2-10}$-alkinyl groups may each be linear or branched and may optionally be substituted with 1, 2, 3, 4 or 5 substituents independently selected from the group consisting of F, Cl, Br, COOH, COOC$_{1-4}$-alkyl, —CN, —OH, —SH, —O—$C_{1-2}$-alkyl, —S—$C_{1-2}$-alkyl and —$NH_2$;

the aforementioned $C_{3-8}$-cycloalkyl groups may each optionally be substituted with 1, 2, 3, 4 or 5 substituents independently selected from the group consisting of F, Cl, Br, —CN, —OH, —SH, —$C_{1-5}$-alkyl, —O—$C_{1-2}$-alkyl, —S—$C_{1-2}$-alkyl and —$NH_2$;

the aforementioned heterocycloalkyl groups each comprise a 4-, 5-, 6- or 7-membered ring containing 1 or 2 heteroatoms independently selected from the group consisting of oxygen, sulfur and nitrogen, and may optionally be substituted with 1, 2, 3, 4 or 5 substituents independently selected from the group consisting of F, Cl, Br, —CN, —OH, —SH, —$C_{1-5}$-alkyl, —O—$C_{1-2}$-alkyl, —S—$C_{1-2}$-alkyl and —$NH_2$;

the aforementioned aryl groups each independently denote a phenyl, anthracenyl or naphthyl group, which optionally may be substituted with 1, 2, 3, 4 or 5 substituents independently selected from the group consisting of F, Cl, Br, I, —$CF_3$, —$OCF_3$, —$SCF_3$, C(=O)$C_{1-5}$-alkyl,

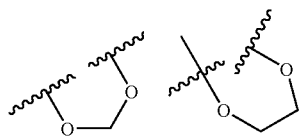

—$NO_2$, cyclohexyl, —$SF_5$, —CN, —OH, —SH, —$C_{1-5}$-alkyl, —O—$C_{1-5}$-alkyl, —S—$C_{1-5}$-alkyl, —C(=O)—OH, —O(C=O)$C_{1-2}$-alkyl, —C(=O)—OC$_{1-5}$-alkyl, —$NH_2$, —N(H)($C_{1-5}$-alkyl), —N($C_{1-5}$-alkyl)($C_{1-5}$-alkyl), —C(=O)$NH_2$, —C(=O)N(H)($C_{1-5}$-alkyl), —C(=O)N($C_{1-5}$-alkyl)($C_{1-5}$-alkyl), —S(=O)$_2NH_2$, —S(=O)$_2$N(H)($C_{1-5}$alkyl), —S(=O)$_2$N($C_{1-5}$-alkyl)($C_{1-5}$-alkyl), —S(=O)$_2$-phenyl, —S(=O)$_2$—$C_{1-5}$-alkyl, phenyl, phenoxy, benzyl, benzyloxy, thiophenyl (thienyl), furanyl and pyridinyl; and the aforementioned heteroaryl groups each independently denote a 5- or 6-membered aromatic ring containing 1, 2 or 3 heteroatoms independently selected from the group consisting of oxygen, sulfur and nitrogen, and may optionally be substituted with 1, 2, 3, 4 or 5 substituents independently selected from the group consisting of F, Cl, Br, I, —$CF_3$, —$OCF_3$, —$SCF_3$, —$SF_5$, —CN, —OH, —SH, —$C_{1-5}$-alkyl, —O—$C_{1-5}$-alkyl, —S—$C_{1-5}$-alkyl, —C(=O)—OH, —C(=O)—OC$_{1-5}$-alkyl, —$NH_2$, —N(H)($C_{1-5}$-alkyl), —N($C_{1-5}$-alkyl)($C_{1-5}$-alkyl), —C(=O)$NH_2$, —C(=O)N(H)($C_{1-5}$-alkyl), —C(=O)N($C_{1-5}$-alkyl)($C_{1-5}$-alkyl), —S(=O)$_2NH_2$, —S(=O)$_2$N(H)($C_{1-5}$-alkyl), —S(=O)$_2$N($C_{1-5}$-alkyl)($C_{1-5}$-alkyl), —S(=O)$_2$-phenyl, —S(=O)$_2$—$C_{1-5}$-alkyl, phenyl, phenoxy, benzyl, thiophenyl (thienyl), furanyl and pyridinyl;

or a pharmaceutically acceptable salt thereof.

2. A compound according to claim 1, wherein said compound is in the form of a mixture of stereoisomers.

3. A compound according to claim 2, wherein said mixture is a racemic mixture.

4. A compound according to claim 1, wherein said compound is in the form of an isolated stereoisomer.

5. A compound according to claim 1, wherein $R^1$, $R^2$, $R^3$ and $R^4$ each independently denote H, F, Cl, Br, I, —CN, —$NR^7R^8$, —$OR^9$, —$SR^{10}$, $C_{1-4}$-alkyl, $C_{2-4}$-alkenyl or $C_{2-4}$-alkinyl;

$R^5$ denotes —(CHR$^6$)$_n$—$R^{25}$, wherein n=1, 2 or 3;

$R^6$ denotes H or $C_{1-6}$-alkyl, and $R^{25}$ denotes aryl or heteroaryl;

$R^7$ and $R^8$ each independently denote H, —C(=O)$R^{15}$ or $C_{1-4}$-alkyl, or $R^7$ and $R^8$ together with the nitrogen atom to which they are bound form a morpholine, piperidine or pyrrolidine ring; and $R^9$, $R^{10}$ each independently denote H, $C_{1-4}$-alkyl, $C_{2-4}$-alkenyl, $C_{2-4}$-alkinyl, $C_{3-8}$-cycloalkyl, —($C_{1-2\text{ or }3}$-alkylene)-$C_{3-8}$-cycloalkyl, heterocycloalkyl, —($C_{1,\ 2\ or\ 3}$-alkylene)-heterocycloalkyl, aryl, heteroaryl, —($C_{1,\ 2\ or\ 3}$-alkylene)-aryl or —($C_{1,\ 2\ or\ 3}$-alkylene)-heteroaryl;

wherein the aforementioned $C_{1-10}$-alkyl, $C_{2-10}$-alkenyl and $C_{2-10}$-alkinyl groups each independently may be linear or branched and may optionally be substituted with 1, 2, 3, 4 or 5 substituents independently selected from the group consisting of F, Cl, Br, —CN, COOH, COOC$_{1-4}$-alkyl, —OH, —SH, —O—$C_{1-2}$-alkyl, —S—$C_{1-2}$-alkyl and —$NH_2$;

the aforementioned $C_{1-4}$-alkyl, $C_{2-4}$-alkenyl and $C_{2-4}$-alkinyl groups each independently may be linear or branched and may optionally be substituted with 1, 2, 3, 4 or 5 substituents independently selected from the group consisting of F, Cl, Br, —CN, —OH, —OCH$_3$ and —$NH_2$;

the aforementioned $C_{3-8}$-cycloalkyl groups each may optionally be substituted with 1, 2, 3, 4 or 5 substituents independently selected from the group consisting of F, Cl, Br, —CN, —OH, —CH$_3$, —$C_2H_5$, —OCH$_3$ and —$NH_2$;

the aforementioned heterocycloalkyl groups each comprise a 4-, 5-, 6- or 7-membered ring containing 1 or 2 heteroatoms independently selected from the group consisting of oxygen, sulfur and nitrogen, and may optionally be substituted with 1, 2, 3, 4 or 5 substituents independently selected from the group consisting of F, Cl, Br, —CN, —OH, —CH$_3$, —$C_2H_5$, —OCH$_3$ and $NH_2$;

the aforementioned aryl groups each independently denote a phenyl, anthracenyl or naphthyl group which may optionally be substituted with 1, 2, 3, 4 or 5 substituents independently selected from the group consisting of F, Cl, Br, —CF3, —$OCF_3$, —$SCF_3$,

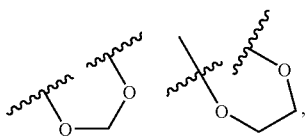

—NO$_2$, —C(=O)C$_{1-2}$-alkyl, cyclohexyl, —O(C=O)C$_{1-2}$-alkyl, —SF$_5$, —CN, —OH, methyl, ethyl, n-propyl, isopropyl, n-butyl, isobutyl, sec-butyl, tert.-butyl, methoxy, ethoxy, —NH$_2$, —N(CH$_3$)$_2$, —N(C$_2$H$_5$)$_2$, phenyl, benzyloxy, phenoxy, benzyl, thiophenyl (thienyl), furanyl and pyridinyl, and the aforementioned heteroaryl groups each independently denote a furanyl, thienyl, (thiophenyl) or pyridinyl group and may optionally be substituted with 1, 2, 3, 4 or 5 substituents independently selected from the group consisting of F, Cl, Br, —CF$_3$, —OCF$_3$, —SCF$_3$, —SF$_5$, —CN, —OH, methyl, ethyl, n-propyl, isopropyl, n-butyl, isobutyl, sec-butyl, tert.-butyl, methoxy, ethoxy, —NH$_2$, —N(CH$_3$)$_2$, —N(C$_2$H$_5$)$_2$, phenyl, phenoxy, benzyl, thiophenyl (thienyl), furanyl and pyridinyl.

6. A compound according to claim 1, wherein R$^6$ denotes H.

7. A compound according to claim 1, wherein R$^6$ denotes CH$_3$.

8. A compound according to claim 1, wherein R$^{25}$ denotes phenyl, pyridyl, thienyl or furyl, in each case unsubstituted or monosubstituted or polysubstituted with CF$_3$, SCF$_3$, C$_{1-4}$-alkyl, Cl, NO$_2$, O-acetyl, OCH$_3$, F, O-phenyl, OCF$_3$, Br, O-benzyl, O-allyl, phenyl, I, CN or OH.

9. A compound according to claim 8, wherein R$^{25}$ denotes 4-trifluoromethylphenyl, 4-SCF$_3$-phenyl, 2-methylphenyl, phenyl, anthracenyl, 4-Cl-phenyl, 4-OCF$_3$-phenyl, 4-n-butylphenyl, 3-(3-CF$_3$-phenoxy)-phenyl, 4-OCHF$_2$-phenyl, 3,5-dimethylphenyl, 3-bromo-4-methoxyphenyl, 4-benzyloxy-3,5-dimethylphenyl, 3-nitrophenyl, 3-methoxy-4-(acetylmethyl)-phenyl, 2,4,5-trimethoxyphenyl, 4-ethylphenyl, 3,4-dichlorophenyl, 2,8,5-trifluorophenyl, 4-phenoxyphenyl, 3-chloro-4-fluorophenyl, 3-benzyloxyphenyl, 3-bromo-4,5-dimethoxyphenyl, 3-fluoro-2-methylphenyl, 2-chloro-3-trifluoromethylphenyl, 3-chloro-2-fluoro-5-trifluoromethylphenyl, 2-fluoro-4-trifluoromethylphenyl, 4-(allyloxy)phenyl, 2-(benzyloxy)-4,5-dimethoxyphenyl, 2-phenylphenyl, 2,3,4-trifluorophenyl, 2-fluoro-5-trifluorophenyl, 4-methoxy-3-methylphenyl, 2-fluoro-3-chlorophenyl, 3,4-difluorophenyl, 2,6-dichlorophenyl, 3-iodophenyl, 3-iodo-4,5-dimethoxyphenyl, 2-cyanophenyl, 4-hydroxyphenyl, 3,4-dimethylphenyl or 3-OCF$_3$-phenyl.

10. A compound according to claim 1, selected from the group consisting of:
benzo[d]isoxazol-3-yl-[1-(4-trifluoromethylphenyl)-ethyl]-amine,
benzo[d]isoxazol-3-yl-[1-(4-trifluoromethylsulfanylphenyl)-ethyl]-amine,
benzo[d]isoxazol-3-yl-(3-methylbutyl)-amine,
(5-fluorobenzo[d]isoxazol-3-yl)-(2-methylbenzyl)-amine,
N4,N4-dimethyl-N3-(3-phenylpropyl)-benzo[d]isoxazol-3,4-diamine,
N3-butyl-N4,N4-dimethyl-benzo[d]isoxazol-3,4-diamine,
anthracen-9-ylmethyl-(4-methoxybenzo[d]isoxazol-3-yl)-amine,
(4-chlorobenzyl)-(4-methoxybenzo[d]isoxazol-3-yl)-amine,
(6-fluorobenzo[d]isoxazol-3-yl)-(3-nitrobenzyl)-amine,
acetic acid-4-[(6-chlorobenzo[d]isoxazol-3-ylamino)-methyl]-2-methoxyphenyl ester,
acetic acid-4-[(6bromobenzo[d]isoxazol-3-ylamino)methyl]-2-methoxyphenyl ester,
benzo[d]isoxazol-3-yl-(3,4-dichlorobenzyl)-amine Benzo[d]isoxazol-3-yl-(2,4,5-trimethoxybenzyl)-amine,
benzo[d]isoxazol-3-yl-(4-ethylbenzyl)-amine,
(6-chlorobenzo[d]isoxazol-3-yl)-(3,4-dichlorobenzyl)-amine,
benzo[d]isoxazol-3-yl-(2,3,5-trifluorobenzyl)-amine,
(6-chlorobenzo[d]isoxazol-3-yl)-(4-phenoxybenzyl)-amine,
(3-chloro-4-fluorobenzyl)-(7-fluorobenzo[d]isoxazol-3-yl)-amine,
benzo[d]isoxazol-3-yl-(4-trifluoromethylbenzyl)-amine,
(7-fluorobenzo[d]isoxazol-3-yl)-(2-methylpentyl)-amine,
N4,N4-dimethyl-N3-(2,3,4-trifluorobenzyl)-benzo[d]isoxazol-3,4-diamine,
N3-(2-fluoro-5-trifluoromethylbenzyl)-N4,N4-dimethyl-benzo[d]isoxazole-3,4-diamine,
N3-(4-methoxy-3-methylbenzyl)-benzo [d]isoxazole-3,4-diamine,
N3-(4-methoxy-3-methylbenzyl)-benzo[d]isoxazole-3,4-diamine,
benzo[d]isoxazol-3-yl-(4-trifluoromethoxybenzyl)-amine,
(5-fluorobenzo[d]isoxazol-3-yl)-(4-trifluoromethoxybenzyl)-amine,
benzo[d]isoxazol-3-yl-(4-trifluoromethylsulfanylbenzyl)-amine,
(4-butylbenzyl)-(6-chlorobenzo[d]isoxazol-3-yl)-amine,
(5-fluorobenzo[d]isoxazol-3-yl)-(4-trifluoromethylsuLfanylbenzyl)-amine,
benzo[d]isoxazol-3-yl-(2-fluoro-4-trifluoromethylbenzyl)-amine,
(7-fluorobenzo[d]isoxazol-3-yl)-(4-trifluoromethoxybenzyl)-amine,
(7-fluorobenzo[d]isoxazol-3-yl)-[3-(3-trifluoromethylphenoxy)-benzyl]-amine,
(4-difluoromethoxybenzyl)-(4-methoxybenzol[d]isoxazol-3-yl)-amine,
(3,5-dimethylbenzyl)-(7-fluorobenzo[d]isoxazol-3-yl)-amine
(3-bromo-4-methoxybenzyl)-(6-fluorobenzo[d]isoxazol-3-yl)-amine,
(3,5-dimethylbenzyl)-(6-fluorobenzo[d]isoxazol-3-yl)-amine,
(4-benzyloxy-3,5-dimethylbenzyl)-(6-fluorobenzo[d]isoxazol-3-yl)-amine,
(4-butylbenzyl)-(6-fluorobenzo[d]isoxazol-3-yl)-amine,
(6-fluorobenzo[d]isoxazol-3-yl)-(4-trifluoromethylsulfanyl-benzyl)-amine,
(3-benzyloxybenzyl)-(6-fluorobenzo[d]isoxazol-3-yl)-amine,
N3-(3,5-dimethylbenzyl)-benzo[d]isoxazole-3,4-diamine,
N3-(4-butylbenzyl)-benzo[d]isoxazole-3,4-diamine,
(5-bromobenzo[d]isoxazol-3-yl)-(4-trifluoromethylsulfanyl-benzyl)-amine,
(3-bromo-4,5-dimethoxybenzyl)-(7-fluorobenzo[d]isaxazole-3-yl)-amine,
(7-fluorobenzo[d]isoxazol-3-yl)-(2-fluoro-4-trifluoromethylbenzyl)-amine, N3-(3-fluoro-2-methylbenzyl)-N4,N4-dimethylbenzo[d]
isoxazole-3,4-diamine,
N3-(2-chloro-3-trifluoromethylbenzyl)-N4, N4-dimethyl-
benzo[d]isoxazole-3,4-diamine,
N3-(3-chloro-2-fluoro-5-trifluoromethylbenzyl)-N4,N4-
dimethyl-benzo[d]isoxazole-3,4-diamine,
(6-fluorobenzo[d]isoxazol-3-yl)-(2-fluoro-4-trifluorom-
ethyl-benzyl)-amine,
(4-allyloxybenzyl)-(6-fluorobenzo[d]isoxazol-3-yl)-
amine Benzo [d]isoxazol-3-yl-(2-benzyloxy-4,5-
dimethoxybenzyl)-amine,
(2-benzyloxy-4,5-dimethoxybenzyl)-(6-chlorobenzo[d]
isoxazol-3yl)-amine
N3-(2-benzyloxy-4,5-dimethoxybenzyl)-N4,N4-dimeth-
ylbenzo[d]isoxazole-3,4-diamine,
N3-biphenyl-2-ylmethyl-N4,N4-dimethylbenzo[d]isox-
azole-3,4-diamine,
(6-fluorobenzo[d]isoxazol-3-yl)-(3-iodobenzyl)-amine,
(2-benzyloxy-4,5-dimethoxybenzyl)-(4-methoxybenzo
[d]isoxazol-3-yl)-amine,
(4-fluorobenzo[d]isoxazol-3-yl)-(3-iodo-4,5-dimethoxy-
benzyl)-amine, 2-[(5-methylbenzo[d]isoxazol-3-
ylamino)-methyl]-benzonitrile,
butyl-[4-(2,2,2-trifluoroethoxy)-benzo[d]isoxazol-3-yl]-
amine,
(3-bromo-4,5-dimethoxybenzyl)-(5-methylbenzo[d]isox-
azol-3-yl)-amine,
4-[(4-chlorobenzo[d]isoxazol-3-ylamino)-methyl]-phe-
nol,
(6-chlorobenzo[d]isoxazol-3-yl)-(3,4-dimethylbenzyl)-
amine,
(4-chlorobenzo[d]isoxazol-3-yl)-(3-chloro-2-fluoroben-
zyl)-amine,
(3,4-difluorobenzyl)-(5-fluorobenzo[d]isoxazol-3-yl)-
amine,
(6-bromobenzo[d]isoxazol-3-yl)-2,6-dichlorobenzyl)-
amine, and
(7-fluorobenzo[d]isoxazol-3-yl)-(3-trifluoromethoxyben-
zyl)-amine,
or a pharmaceutically acceptable salt thereof.

11. A process for producing a substituted benzo[d]isox-
azol-3-yl amine compound, said process comprising:
reacting a starting compound corresponding to formula I

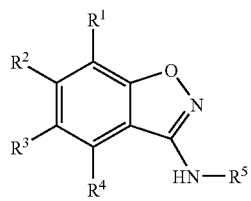

wherein
$R^1$, $R^2$, $R^3$, $R^4$ have the meanings given in claim 1, and
$R^5$ denotes H,
in a reaction medium, in the presence of at least one base,
with a compound corresponding to one of the formulas

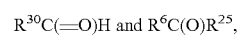

wherein
$R^6$ and $R^{25}$ have the meanings given in claim 1, and
$R^{30}$ denotes
a linear or branched, saturated or unsaturated, unsubsti-
tuted or mono- or polysubstituted aliphatic group, or
an unsubstituted or mono- or polysubstituted aryl or
heteroaryl moiety, which may be condensed with a
monocyclic or polycyclic ring system; or
an unsubstituted or mono- or polysubstituted aryl or
heteroaryl moiety which can be condensed with a
monocydic or polycyclic ring system and which is
bonded via a linear or branched alkylene group;
to form a product compound corresponding to formula I in
which $R^5$ has the meaning given in claim 1, and
optionally isolating or purifying the product compound.

12. A process according to claim 11, wherein the reaction
medium is selected from the group consisting of acetonitrile,
toluene, dimethylformamide, benzene, ethanol, methanol,
DCM, trifluoroacetic acid and mixtures thereof, and the base
is triethylsilane or a metal hydride or metal alcoholate salt
selected from the group consisting of sodium hydride, potas-
sium hydride, potassium tert.-butanolate, sodium tert.-bu-
tanolate, potassium methanolate, sodium methanolate,
sodium ethanolate and potassium ethanolate.

13. A pharmaceutical composition comprising a com-
pound according to claim 1, and at least one pharmaceutically
acceptable auxiliary substance.

14. A method of treating or inhibiting a condition selected
from the group consisting of pain, migraine, anxiety, urinary
incontinence and epilepsy in a subject in need thereof, said
method comprising administering to said subject a therapeu-
tically effective amount of a compound according to claim 1.

15. A method according to claim 14, wherein said condi-
tion is pain selected from the group consisting of acute pain,
chronic pain, neuropathic pain, muscular pain and inflamma-
tory pain.

* * * * *